(12) United States Patent
Avram et al.

(10) Patent No.: US 10,582,960 B2
(45) Date of Patent: Mar. 10, 2020

(54) METHODS AND DEVICES FOR SELECTIVE DISRUPTION OF VISCERAL FAT BY CONTROLLED COOLING

(71) Applicant: The General Hospital Corporation, Boston, MA (US)

(72) Inventors: Matthew M. Avram, Boston, MA (US); Richard Rox Anderson, Boston, MA (US); Joshua Tam, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/970,789

(22) Filed: May 3, 2018

(65) Prior Publication Data

US 2018/0250056 A1 Sep. 6, 2018

Related U.S. Application Data

(63) Continuation of application No. 13/574,425, filed as application No. PCT/US2011/024766 on Feb. 14, 2011, now Pat. No. 9,980,765.

(Continued)

(51) Int. Cl.
*A61B 18/02* (2006.01)
*A61F 7/10* (2006.01)
*A61F 7/12* (2006.01)

(52) U.S. Cl.
CPC .............. *A61B 18/02* (2013.01); *A61F 7/10* (2013.01); *A61F 2007/126* (2013.01)

(58) Field of Classification Search
CPC ........ A61B 18/02; A61F 7/10; A61F 2007/126
See application file for complete search history.

(56) References Cited

U.S. PATENT DOCUMENTS

| 5,143,063 A | 9/1992 | Fellner |
| 5,507,790 A | 4/1996 | Weiss |

(Continued)

OTHER PUBLICATIONS

Gilbert P. Gradinger et al., "Abdominoplasty", in The Art of Aesthetic Surgery: Principles and Techniques (Foad Nahai d., 1st ed. 2005).

(Continued)

*Primary Examiner* — Lindsey G Wehrheim
(74) *Attorney, Agent, or Firm* — Saul Ewing Arnstein & Lehr LLP; Brian R. Landry

(57) ABSTRACT

In one aspect, the present invention provides a method of cooling to produce selective disruption of visceral fat tissue in a non-infant human subject comprising infusing a cooled fluid into the abdominal or peritoneal cavity, or into other parts of the body containing visceral fat, to cool the proximal tissue sufficiently to selectively disrupt lipid-rich cells therein, for example, to promote subsequent damage and absorption of lipid-rich cells by the body without producing unwanted effects in non-lipid-rich cells; e.g., without injury to internal organ tissues that could otherwise produce life-threating risks. The cooled fluid can be infused using a catheter arrangement. The cooled fluid can be retained within the abdominal category for a particular duration, and then drained using the catheter arrangement. In certain embodiments, the cooled fluid can be simultaneously introduced into the abdominal cavity and drained therefrom.

20 Claims, 20 Drawing Sheets

Related U.S. Application Data

(60) Provisional application No. 61/304,609, filed on Feb. 15, 2010.

(56) References Cited

U.S. PATENT DOCUMENTS

| | | | |
|---|---|---|---|
| 5,769,879 | A | 6/1998 | Richards |
| 6,962,601 | B2 | 11/2005 | Becker |
| 7,367,341 | B2 | 5/2008 | Anderson |
| 7,422,601 | B2 | 9/2008 | Becker |
| 7,507,234 | B2 | 3/2009 | Utley |
| 2005/0203598 | A1 | 9/2005 | Becker |
| 2005/0251120 | A1 | 11/2005 | Anderson |
| 2007/0010861 | A1* | 1/2007 | Anderson ............ A61B 5/415 607/96 |
| 2007/0106247 | A1 | 5/2007 | Burnett |
| 2009/0118722 | A1* | 5/2009 | Ebbers ............ A61B 18/02 606/21 |
| 2009/0255276 | A1 | 10/2009 | Kasza |
| 2010/0152880 | A1 | 6/2010 | Boyden |
| 2014/0200511 | A1 | 7/2014 | Boyden |
| 2017/0274011 | A1 | 9/2017 | Garibyan |

OTHER PUBLICATIONS

Laverson S., Improving abdominoplasty results: reconstruction of the linea alba sulcus by direct excision, Aesthetic Surgery Journal 26: 682-6 (2006).

Brink R., Abdominoplasty with direct resection of deep fat, Plastic and Reconstructive Surgery 123(5): 1597-1603 (2008).

Yuji Yamamoto et al., Adipose Depots Possess Unique Developmental Gene Signatures, Obesity 18(5) 872-78 (May 2010).

Ding, J., et al., "The association between non-subcutaneous adiposity and calcified coronary plaque: A substudy of the Multi-Ethnic Study of Atherosclerosis", Am J Clin Nutr.; 88(3): 645-650, Sep. 2008.

Fox, C. S., et al., "Abdominal Visceral and Subcutaneous Adipose Tissue Compartments—Association With Metabolic Risk Factors in the Framingham Heart Study", Circulation, Jul. 2007.

Ash, S. R, "Chronic Peritoneal Dialysis Catheters: Overview of Design, Placement, and Removal Procedures", 16(4) Interventional Nephrology and Dialysis 323-34 (2003).

Garaulet M., et al., "Relationship between fat cell size and number and fatty acid composition in adipose tissue from different fat depots in overweight/obese humans", 30(6) Int J Obes, 899-905 (2006).

Levin, B. A., "A pilot study of ice-slurry application for inducing laparoscopic renal hypothermia", 99 BJU International 166-70 (2006).

International Search Report and Written Opinion, International Patent Application No. PCT/US2011/024766, dated Apr. 12, 2011.

* cited by examiner

*Subcutaneous (10x)*

*Visceral (10x)*     *Visceral (10x plane-polarized light)*

Subcutaneous (10x) | Visceral (10x)

Subcutaneous (10x) | Visceral (10x)

needle-shaped structures visible along edges of opaque stuff about the same as 19C (image quality not as good at 4C due to condensation on the glass)

*Visceral (20x)*                *Visceral (20x)*

*Subcutaneous Fat at 37°C*        *Visceral Fat at 37°C*

Subcutaneous Fat at 20°C         Visceral Fat at 20°C

Subcutaneous Fat at 15°C         Visceral Fat at 15°C

METHODS AND DEVICES FOR SELECTIVE DISRUPTION OF VISCERAL FAT BY CONTROLLED COOLING

CROSS-REFERENCE TO RELATED APPLICATION

This application is a continuation under 35 U.S.C. § 120 of U.S. patent application Ser. No. 13/574,425, filed Mar. 15, 2013, which is a national phase entry application under 35 U.S.C. § 371 of International Application No. PCT/US2011/024766, filed Feb. 14, 2011, which claims priority to U.S. Provisional Patent Application Ser. No. 61/304,609, filed Feb. 15, 2010. The entire content of each of these applications is hereby incorporated herein by reference in its entirety.

BACKGROUND

Visceral fat (including intra-abdominal fat) is fat that surrounds the internal organs, primarily in the abdomen. Visceral fat can include omental fat, which is located on the sheetlike omentum that hangs in front of the intestines within the peritoneal cavity, fat surrounding organs such as the liver, pancreas, spleen, gut, bladder, reproductive organs and kidneys, etc. Visceral fat is qualitatively different from subcutaneous fat, which lies just below the skin and is generally considered to be both less dangerous (with respect to general health) and easier to lose than visceral fat.

Various studies in the literature suggest that an excess of visceral fat can contribute to a variety of health issues, such as heart disease, stroke, type 2 diabetes, etc. Location of such fat can be as important with respect to adverse health effects as the amount of such excess fat. Secondary problems arising from excess body weight stemming from an excess of fat include musculoskeletal problems, arthritis, psychological issues with self-image, and difficulty exercising. The liver also can metabolize visceral fat and release it into the bloodstream as cholesterol. It has been observed that surgical removal of visceral fat in experimental animal models can lead to alleviation of diabetic symptoms, whereas removal of subcutaneous fat has no such discernible effect on health.

Various superficial techniques have been developed for reducing subcutaneous fat, which is generally located just below the skin surface. For example, non-invasive techniques for reducing subcutaneous fat using radiant energy are described in U.S. Pat. Nos. 5,143,063, 5,507,790, and 5,769,879.

Various observations suggest that fat tissue may be sensitive to cold-induced injury. Exposure to low temperatures can cause inflammatory damage and fat necrosis in subcutaneous fat tissue (cold panniculitis). Lipid crystallization in fat cells may be a mechanism by which such disruption of the fatty tissue occurs. For example, infants and young children have been observed to be particularly susceptible to cold panniculitis. This may result from the higher concentration of saturated lipids in fat tissue of children, which tend to have higher melting points. A method and apparatus for reducing subcutaneous fat using contact cooling is disclosed in U.S. Pat. No. 7,367,341. This patent describes disruption of subcutaneous fatty tissue by cooling the fatty tissue below normal body temperature using contact cooling methods and apparatus. A portion of the cooled fatty tissue is gradually resorbed by the body, resulting in a reduction in the amount of subcutaneous fat in the treated area.

However, such techniques for reducing subcutaneous fat are generally not applicable to the deeper visceral fat that is further below the skin surface and is often surrounded by bodily organs. Mechanical removal techniques, such as liposuction, are also not desirable for removing visceral fat because of the significant risks involved with mechanical damage to the organs and tissue structures in the abdomen, such as the peritoneum. There may also be a risk of peritonitis, a serious infection of the abdominal cavity.

Accordingly, visceral fat is harder to remove or reduce than subcutaneous fat in part because it is located deeper within the body. The currently accepted techniques for reducing visceral fat are non-specific approaches, such as diet and exercise.

Techniques have been developed for safely introducing liquids into the peritoneal or abdominal cavity, which is a region of the abdomen located below the lungs and stomach that is lined with a membrane called the peritoneum. For example, a peritoneal dialysis (PD) procedure can be performed to assist the body in removing waste if the kidney function is impaired. A PD procedure includes introduction of a soft tube (e.g., a catheter) into the peritoneal cavity, generally through a small slit formed close to the navel. The abdominal cavity is then filled with a dialysis solution, which is allowed to remain in the body for an extended period of time, referred to as a 'dwell time,' that is often between about 4 and 6 hours. During this treatment, the peritoneal membrane allows waste products and extra fluid to pass from the blood into the dialysis solution. The dialysis solution is subsequently drained, which also removes wastes along with the drained fluid. The time needed to fill or drain the dialysis solution is typically about 30 to 40 minutes.

The dialysis solution used in PD procedures is heated to approximately body temperature prior to pumping it into the abdominal cavity. Such heating is required for this procedure to maintain a substantially uniform normal body temperature in the abdomen during the PD procedure.

It would be desirable to selectively and controllably cool the abdominal cavity, and to damage fatty tissue such as adipocytes of the intra-abdominal (visceral) fatty tissue without causing injury to the surrounding tissue and organs. Both health and cosmetic benefits may result from reduction of fatty tissue. However, current methods for subcutaneous fat reduction, such as liposuction, involve invasive procedures with potentially life-threatening risks (e.g., excessive bleeding, mechanical damage to internal organ tissues, etc.). Further, such procedures may not be suitable for physically removing visceral fat, which may be more viscous and rigid than subcutaneous fat.

SUMMARY OF THE INVENTION

Adipose tissue comprising lipid-rich cells in visceral fat may be selectively disrupted without causing injury to the surrounding non lipid-rich tissue (e.g., internal organs) by controlled cooling of the fatty tissue, which can be referred to as cryolipolysis. Embodiments of the present disclosure can address the above problems by providing a method and apparatus for disrupting visceral fat using controlled cooling. Thus a targeted procedure can be provided for reducing the amount of visceral fat in an individual, which can lead to improved health and physical appearance.

Without being bound by theory, the invention is based, at least in part, on the discovery that selective disruption of lipid-rich cells results from localized crystallization of highly saturated fatty acids upon cooling at temperatures that do not induce crystallization of highly saturated fatty acids in non lipid-rich cells. The crystals may rupture the bilayer membrane of lipid-rich cells, causing necrosis. Thus, damage of non lipid-rich cells, such as organ or dermal cells, can be avoided at temperatures that induce crystal formation in lipid-rich cells. It is also believed that cooling induces lipolysis (e.g., metabolism) of lipid-rich cells, further enhancing the reduction in subcutaneous adipose tissue. Lipolysis may be enhanced by local cold exposure inducing stimulation of the sympathetic nervous system.

In one aspect, the present invention provides a method of cooling to produce selective disruption of visceral fat tissue in a non-infant human subject comprising infusing a cooled fluid into the abdominal or peritoneal cavity, or into other parts of the body containing visceral fat, to cool the proximal tissue sufficiently to selectively disrupt lipid-rich cells therein, for example, to promote subsequent damage and absorption of lipid-rich cells by the body without producing unwanted effects in non-lipid-rich cells; e.g., without injury to internal organ tissues that could otherwise produce life-threating risks. The cooled fluid can be infused using a catheter arrangement. The cooled fluid can be retained within the abdominal category for a particular duration, and then drained using the catheter arrangement. In certain embodiments, the cooled fluid can be simultaneously introduced into the abdominal cavity and drained therefrom.

In further embodiments, the cooled fluid can be provided within a sealed envelope or pouch that may be placed proximal to the fatty tissue using a catheter or other cannula or the like. The envelope can be configured to expand and contact at least a portion of the nearby fatty tissue when the cooled fluid is introduced into it from an external source. The cooled fluid can be introduced into the envelope and allowed to remain for a particular duration before being aspirated from the envelope, and the envelope can then be withdrawn from the body. In some embodiments, the cooled fluid may be continuously introduced and withdrawn from the envelope, which may facilitate more precise control of the temperature within the envelope over time.

In another aspect, the invention provides an apparatus for selectively disrupting lipid-rich cells in a non-infant human subject by cooling. The apparatus can include a fluid reservoir, a temperature control arrangement configured to cool at least a portion of the fluid to a temperature below normal body temperature (e.g., to a temperature below about 25° C.), and a catheter or cannula connected to the fluid source using, e.g., a tube, hose, or other fluid conduit. The apparatus can be configured to introduce cooled fluid at one or more particular temperatures to an internal region of the body proximal to body tissue that includes visceral fat or other lipid-rich tissue via the catheter or cannula. The apparatus may also include a second fluid conduit connected to the cannula or catheter configured to withdraw fluid after it is introduced into the tissue region. For example, the apparatus can be configured to simultaneously introduce cooled fluid into the internal region and withdraw such fluid to provide a continuous flow of the cooled fluid through a portion of the internal region.

In certain embodiments, the apparatus further includes an envelope or pouch that may be provided at the internal region using the catheter or cannula. The envelope can be configured to expand, unroll, spread apart, or the like when fluid is introduced into the envelope via the cannula. In this manner, cooled fluid can thus be provided in the internal region proximal to fatty tissue to cool the tissue without directly contacting internal body tissues because it is contained within the envelope. The envelope can be formed using any biocompatible material that may advantageously be flexible or pliant such as, e.g., silicone rubber, a polymer, or the like.

These and other objects and embodiments are described in the following Detailed Description and are within the scope of the invention.

BRIEF DESCRIPTION OF THE DRAWINGS

So that those having ordinary skill in the art to which the present invention appertains will more readily understand how to make and use the same, reference may be had to the drawings wherein.

Although the present invention will now be described in detail with reference to the figures, it is done so in connection with the illustrative embodiments and is not limited by the particular embodiments illustrated in the figures.

DETAILED DESCRIPTION

The present invention provides a method and apparatus for locally disrupting adipose tissue, e.g., visceral fat, comprising providing a fluid or other cooling means into the abdominal cavity at a temperature sufficiently low to selectively disrupt lipid-rich cells, wherein the temperature does not produce unwanted effects in non-lipid-rich cells.

Figure 1A:
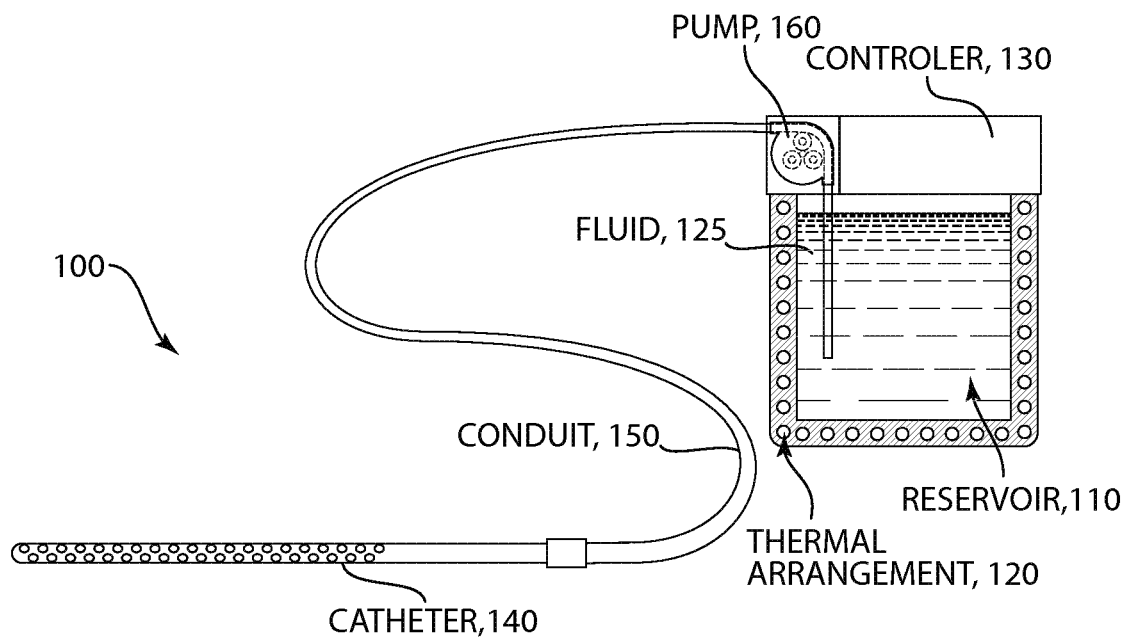
FIGS. 1A-1B are schematic illustrations of an exemplary apparatus configured to cool visceral fat tissue.

An apparatus 100 in accordance with embodiments of the present invention is shown in FIG. 1A. The exemplary apparatus 100 includes a reservoir 110 and optionally a thermal arrangement 120 configured to cool and optionally heat a fluid 125 held in the reservoir 110. For example, the thermal arrangement 120 can be configured to cool the fluid 125 while it is held in the reservoir 110. The reservoir 110 can optionally be insulated to facilitate maintenance of a particular temperature and reduce thermal communication of the fluid 125 with the local environment. A controller 130 can be provided to control the thermal arrangement 120, for example, to maintain the fluid 125 in the reservoir at a particular temperature.

The apparatus 100 shown in FIG. 1A includes a catheter 140 and a conduit 150 provided between the reservoir 110 and the catheter 140. The catheter 140 includes at least one lumen configured to allow the fluid 125 to pass through at least a portion of the catheter 140. The conduit can be arranged to provide a hydraulic communication between the reservoir 110 and the catheter 140, e.g., to facilitate flow of the fluid 125 from the reservoir 110 and into the catheter 140. The apparatus 100 can further include a pumping arrangement 160 configured to pump the fluid 125 from the reservoir 110 through the conduit 150 and into the catheter 140. At least a portion of the conduit 150 can be formed of a flexible material to facilitate movement and positioning of the catheter 140 relative to the rest of the apparatus 100. The pumping arrangement 160 can include, for example, a conventional fluid pump capable of producing a suitable range of flow rates.

In certain embodiments, the thermal arrangement 120 can be in thermal contact with at least a portion of the conduit 150 (in addition to, or instead of, being in thermal contact with the reservoir 110). The thermal arrangement 120 can be configured to cool, cool further, and/or warm the fluid 125 as it passes through the conduit 150.

The controller 130 can include one or more processors, a data storage arrangement, and an interface to allow the controller 130 to affect operation of the pumping arrangement 160 and/or the thermal arrangement 120. For example, the controller 130 can be used to cool and/or heat the fluid 125 to one or more particular temperatures over time, e.g., based on certain predetermined parameters and/or signals received from one or more sensors. Such sensors (not shown in FIG. 1) can be provided on, within, and/or proximal to the catheter 140, the conduit 150, and/or the reservoir 110. Such sensors can include any conventional thermal sensors such as, e.g., a thermocouple, a thermistor, a resistance temperature detector (RTD), or the like. The sensor(s) can be provided in communication with the controller 130, e.g., configured to provide one or more signals to the controller 130 based on a measured temperature. The controller 130 can also be configured to control the rate of fluid flow provided through the conduit 150, e.g., by controlling the speed or other parameters of the pumping arrangement 160.

Figure 1B:
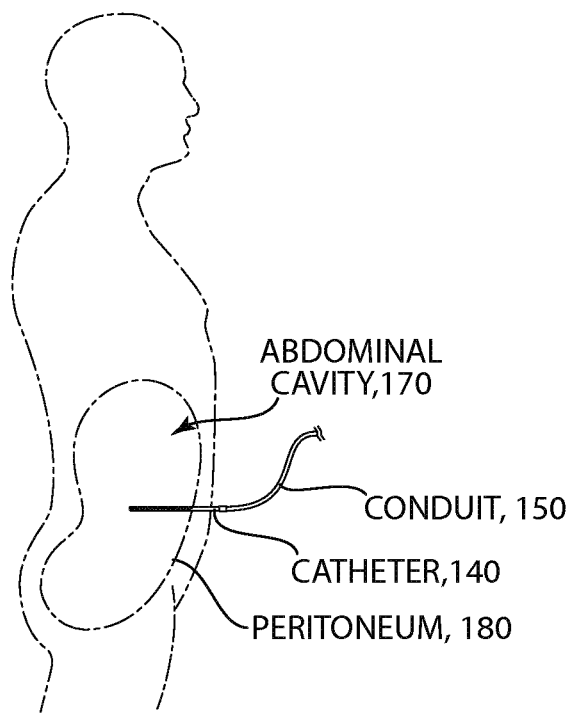

The exemplary apparatus can be used to disrupt and/or reduce the presence of visceral fat present in regions of the human body by controlled cooling of the fatty tissue. For example, a distal end or portion of the catheter 140 can be configured to be inserted through the peritoneum into the peritoneal or abdominal cavity 170, as shown in FIG. 1B. The design of the catheter 140 and method of insertion can be similar to those used in conventional peritoneal dialysis procedures well-known in the art. A conventional laparoscopic probe or element can be provided with the catheter 140 to guide the insertion and/or placement of the catheter 140 within the peritoneal cavity 170.

After insertion of the catheter 140, cooled fluid can be pumped from the reservoir or another source through the catheter and into the abdominal cavity 170. The cooled fluid 125 can be allowed to remain in the abdominal cavity 170 for a particular period of time to achieve a desired degree of cooling of a portion of the visceral fat tissue located therein.

The catheter 140 can include a single opening at the distal end thereof to direct flow of the cooled fluid 125 into and/or out of the abdominal cavity 170. Alternatively, the catheter 140 can have a plurality of holes along the length thereof, as shown in FIG. 1A. Such a catheter 140 with multiple holes can facilitate dispersion of the cooled fluid 125 into a broader internal region of the body such as the abdominal cavity 170, e.g., over a larger portion of the omentum that contains visceral fat. A catheter 140 with several holes can also facilitate draining or removal of the fluid 125 from the abdominal cavity 170.

When the fatty tissue is sufficiently cooled, or during the cooling procedure, the pump arrangement 160 can be reversed, or a second pumping arrangement or further portion of the pumping arrangement 160 can be activated, to remove some, most, or substantially all of the fluid 125 from the abdominal cavity 170 through the catheter 140 and conduit 150. In this manner, a controlled cooling of the abdominal visceral fat can be achieved. Such cooling can disrupt the fatty tissue, a portion of which may then be absorbed by the body over time. Further details regarding the cooling fluid and process parameters are described in more detail below.

Figure 2:
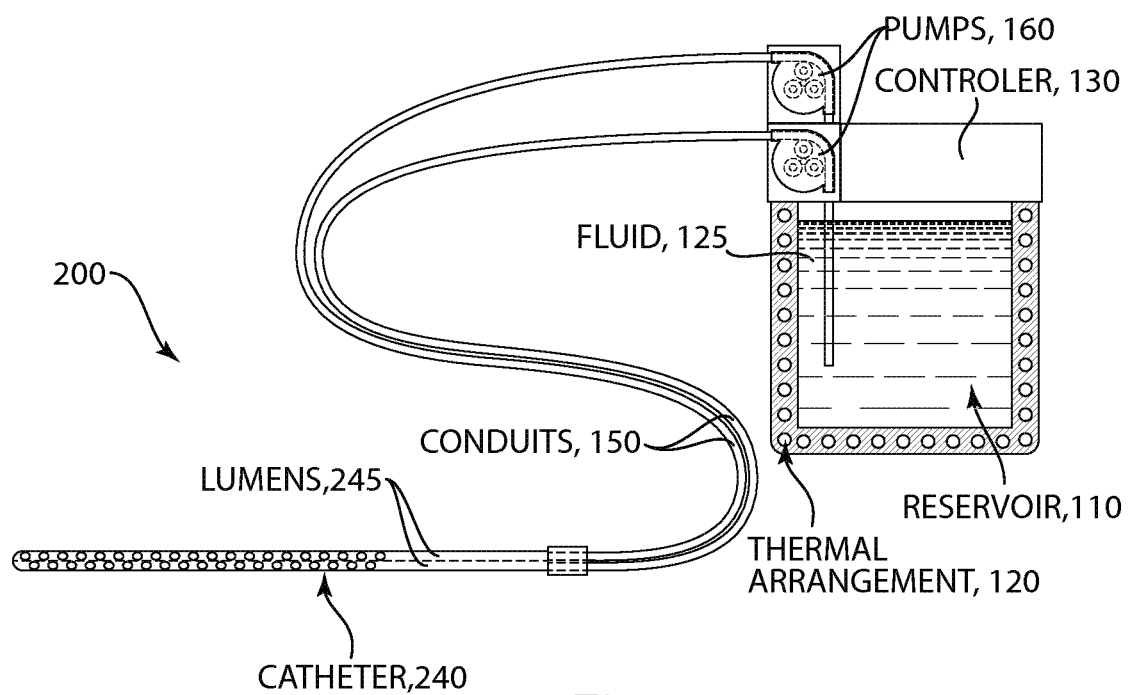
FIG. 2 is a schematic illustration of a further exemplary apparatus configured to cool visceral fat tissue.

A further exemplary apparatus 200 for cooling and/or disrupting the structure of visceral fat is illustrated in FIG. 2. The apparatus 200 includes a reservoir 110, thermal arrangement 120, and pumping arrangement 160, which may be similar to those shown in FIG. 1A. The apparatus 200 further includes a catheter 240 that is provided with at least two separate lumens 245.

The pumping arrangement 160 can include two or more pumps, where each of the lumens 245 of the catheter 240 illustrated in FIG. 2 can be connected to a separate pump of the pumping arrangement 160 through a separate channel or conduit 150. Alternatively, the pumping arrangement 160 can include a single pump with two separate chambers, with each chamber connected to a separate lumen 245 of the catheter 240 through a separate conduit 150. Advantageously, the two pump chambers or two pumps are independently controllable. At least a portion of the conduits 150 is advantageously made of a flexible material, and they may be provided as separate tubes or both conduits 150 can be provided, for example, within a single tubular housing or the like.

One or more holes can be provided through the wall of the catheter 240 into each of the lumens 245 and/or an opening can be provided at a distal end of the catheter end 240 to facilitate passage of a fluid between each lumen 245 and a volume or region external to the catheter 245. For example, the exemplary catheter 240 shown in FIG. 2 includes holes provided through the catheter wall along a distal portion of the catheter into a first lumen, and further holes provided closer to the proximal end of the catheter 240 that communicate with a second lumen.

The catheter 240 can optionally include different numbers and/or configurations of lumens 245 and/or holes. For example, in one exemplary embodiment the catheter 240 can be provided with a divider across an interior diameter of a central hollow core that extends substantially along the total length of the catheter 240, thereby dividing the central core into two longitudinal lumens 245, where each lumen 245 can extend substantially along the entire length of the catheter 240. One or more holes can be provided at different locations of the catheter wall to facilitate passage of a fluid between each lumen 245 and a volume or region external to the catheter 245. In one exemplary embodiment, one or more rows of holes can be provided on opposite sides of the catheter wall along the length of the catheter 240, with each row or set of rows communicating with one of the lumens 245. The particular configuration of a catheter 240 can be selected based on such factors as desired flow rates, dispersion or localization of the supplied and/or withdrawn fluid, etc.

In use, the catheter 240 shown in FIG. 2 can be inserted into the abdominal cavity 170 as shown in FIG. 1B, or otherwise positioned such that a portion of the catheter 240 is proximal to the region of fatty tissue to be cooled. Cooled fluid 125 can be pumped from the reservoir 110 through a first conduit 150 into a first lumen 245 of the catheter 240 using the pump arrangement 160, such that it flows out through the holes at the distal end of the catheter 240 and into the abdominal cavity 170 or other location proximal to the catheter 240. After a particular amount of fluid 125 has been directed into the desired location and allowed to remain for an appropriate time interval, the fluid 125 (or a portion thereof) can be removed by suctioning or withdrawing it through the holes and through a second lumen 245 of the catheter 240 and second conduit 150 using the pump arrangement 160. The withdrawn fluid 125 can be collected in a storage or waste container for recycling or to be discarded.

In a further embodiment, the apparatus 200 shown in FIG. 2 can be operated in a continuous flow mode. Such procedure can be similar to that used for a conventional continuous recirculating peritoneal dialysis (CRPD) procedure. For example, after the catheter 240 is inserted at least partially into the abdominal cavity 170 (or other location in the subject's body), cooled fluid 125 can be pumped into the abdominal cavity 170 through the holes in the first lumen 245 of the catheter 240. Simultaneously, further fluid 125 can be withdrawn from the abdominal cavity 170 through the holes leading into the second lumen 245 of the catheter 240. An optional delay can be provided after fluid 125 is introduced into the abdomen before withdrawing a portion of the fluid 125. For example, a particular volume of fluid 125 can be maintained in the abdominal cavity 170 during all or a portion of the cooling procedure. The total volume of fluid 125 introduced into the abdominal cavity 170 or other region of the subject's body can also be controllably varied during the procedure in this manner. For example, the volume of introduced fluid 125 within the subject's body can initially increase to a particular volume, be maintained at that volume by matching the flow rate of new fluid 125 being introduced to the flow rate of fluid 125 being removed, and then decreasing the amount of fluid 125 in the abdominal cavity 170 by withdrawing the fluid 125 faster than it is being introduced (e.g., by stopping introduction of fluid 125 from the reservoir 110 at a particular time of the procedure while continuing to withdraw the fluid 125).

The flow rates into and out of the abdomen can be controlled by controlling the operation of the pumping arrangement 160. For example, the inlet and outlet flow rates can be matched to maintain a constant amount of fluid 125 within the abdominal cavity 170 during the continuous-flow procedure (e.g., except for the initial and final portions of the treatment). Alternatively, the withdrawal rate of fluid 125 can be set to be slightly greater than the inlet flow rate after an initial amount of fluid 125 has been provided in the abdominal cavity 170 or other location in the subject's body. This can lead to a gradual lessening of the fluid volume in the abdominal cavity 170 as the surrounding tissue is cooled by the fluid 125. A double-lumen catheter design that can be used in such a conventional CRPD procedure may also be used in certain embodiments of the present invention.

Control techniques based on feedback mechanisms can be employed to facilitate monitoring and control of temperatures in the abdominal cavity 170 or other location where fatty tissue is being cooled (e.g., the fatty tissue, adjacent organs, etc.). For example, one or more temperature sensors can be provided at various locations of the apparatus 100, 200 shown in FIG. 1A or FIG. 2 to improve thermal control of the fat cooling procedure. Such temperature sensors can include, for example, resistive elements (such as thermistors or RTDs), thermocouples (e.g., type T, E, J, K, G, C, D, R, S, or B thermocouples) and the like. The use of thermistors may be particularly advantageous because of their high sensitivity to temperature changes within a predetermined range.

For example, one or more temperature sensors can be provided on or within the catheter 140, 240, e.g., near the distal and/or proximal ends thereof. Temperature sensors can also be provided in and/or proximal to the conduits 150 connecting the catheter 140, 240 to the pump arrangement 160. Temperature sensors may also be provided on or within the reservoir 110 that holds the cooled fluid 125. Flow sensors may also be placed in the conduits 150 to monitor flow rates of the fluid 125 into and/or out of the abdominal cavity 170 or other region of the subject's body.

In accordance with an embodiment of the invention, one or more thermistors with a large negative temperature coefficient of resistance ("NTC") can be used. Advantageously, a thermistor or other temperature sensor used in embodiments of the invention may have a working temperature range that includes temperatures between about −15° C. and about 40° C. A thermistor that includes active elements of polymers or ceramics may be used, for example, a ceramic thermistor may be preferable because such thermistors tend to be thermally stable and can provide reproducible temperature measurements. Temperature sensors can be encapsulated in a protective material, such as glass or the like. Such protective material can be provided as a thin shell and/or have a relatively high thermal conductivity to improve detection of time-varying temperature changes.

Temperature sensors as described herein can be used to monitor local temperatures of the tissue being cooled, e.g., tissue proximal to the catheter 140, 240. These sensors advantageously communicate with the controller to facilitate control of the amount and extent of cooling that occurs in the abdominal cavity 170 through introduction and removal of the cooled fluid 125. Any one or more of the temperature, inlet flow rate, and/or outlet flow rate can be adjusted based on temperatures and/or flow rates detected at various points in the apparatus 100, 200, e.g., using conventional control algorithms. For example, if simultaneous introduction and withdrawal of fluid 125 to/from the abdominal cavity 170 or other region of the subject's body is being performed, excessive cooling may be indicated if the temperature of the withdrawn fluid 125 falls below a particular level. A feedback mechanism can monitor temperatures within the subject's abdomen to ensure that the temperature therein does not fall below a predetermined minimum temperature. The amount of cooling can be adjusted, e.g., by reducing the flow rates (thus increasing the residence time of the fluid and allowing the body to warm up slightly) and/or by increasing the temperature of the fluid being pumped into the abdomen. Similarly, flow rates can be increased and/or the inlet fluid temperature can be decreased if the sensors indicate that there is insufficient cooling.

Other sensors and feedback mechanisms can be used to monitor and control the cooling process. For example, crystal formation in the visceral fat may be measured using ultrasound (acoustical) imaging, optical signals, and/or mechanical measurements. Sensors configured to detect crystallization based on such properties are known in the art, and may be provided on the catheter or introduced through the catheter. As described herein below, cooling the visceral fat sufficiently to produce at least some crystallization of the fatty tissue can damage the fat and promote its resorption by the body. Accordingly, using detectable physical properties as a criterion for controlling the amount of cooling applied to the abdominal cavity can improve the effectiveness of the fat disruption methods and apparatus described herein.

In one embodiment, fluid 125 can be heated to approximately normal body temperature or slightly warmer and may then be pumped into the abdominal cavity 170 after sufficient cooling has occurred. This warm fluid 125 can be provided from a second reservoir (not shown) containing the heated fluid, or the thermal arrangement 120 can be used to heat the fluid 125 in the reservoir 110 or while it is in the conduit 150 before it is introduced into the abdominal cavity 170. Such warmed fluid 125 can facilitate a more rapid warming of the tissues and organs in the abdominal cavity 170 after the particular amount of cooling has occurred, which may alleviate discomfort and more quickly restore normal conditions for the surrounding organs.

Figure 3A:
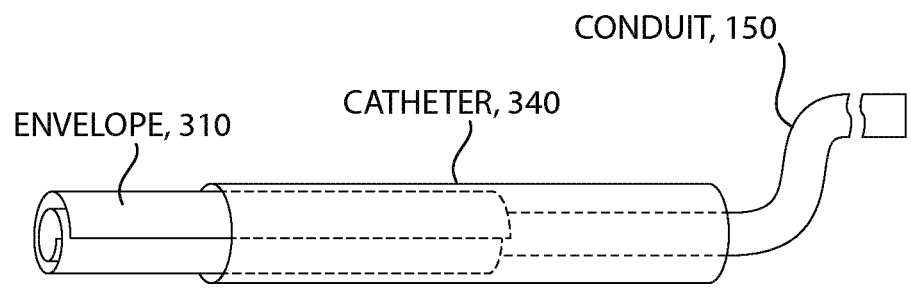
FIGS. 3A and 3B are schematic illustrations of a catheter arrangement that can be used to contain a cooled fluid to cool adjacent tissue.
Figure 3B:
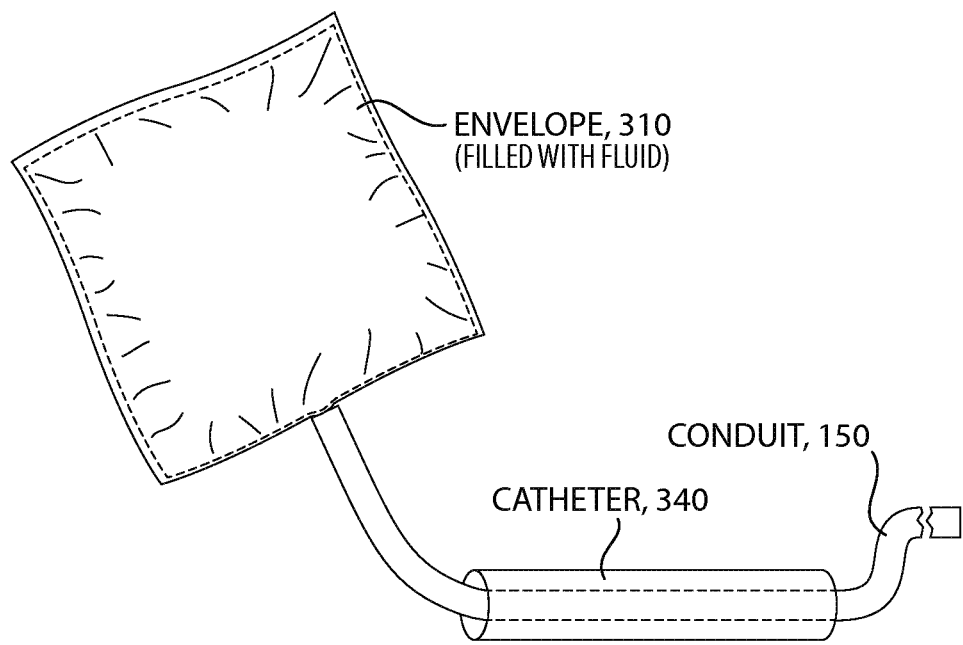

In a further embodiment, illustrated in FIG. 3A, a closed container 310, e.g., a flexible thin envelope or pouch, can be provided in a delivery catheter 340 and introduced into the peritoneal or abdominal cavity 170, e.g. in a rolled-up configuration as shown in FIG. 3A or other collapsed configurations. For example, the envelope 310 may be rolled-up and surrounded by a sheath (not shown) that can be withdrawn after the sheath is introduced into the abdominal cavity 170 through the catheter 340. The envelope 310 can be connected to a lumen of the catheter 340, e.g. at a distal end thereof, or directly to a conduit 150 that passes through the catheter 340 as shown in FIG. 3B. The conduit 150 can be connected to a pumping arrangement 160 and reservoir 110 as illustrated, e.g., in FIGS. 1A and 1n FIG. 2.

Cooled fluid 125 can be pumped through the conduit 150 and into the envelope 310, which may then unroll and/or otherwise expand within the abdominal cavity 170, as illustrated in FIG. 3B. The cooled fluid 125 within the envelope 310 can cool tissue proximal to the expanded envelope 310, e.g., fatty tissue, such that the fluid 125 remains within the envelope 310 and no fluid 125 is in direct contact with the fatty tissue or other organs or tissue within the peritoneal cavity 170 or other internal region of the subject's body. The fluid 125 within the envelope 310 can be withdrawn after a particular cooling period has elapsed. The procedure of introducing cooled fluid 125 into the envelope 310 and then removing it can optionally be repeated for two or more cycles until a total amount of cooling has been achieved. After sufficient cooling has occurred, the emptied envelope 310 can be pulled back into the catheter 340 and the catheter 340 subsequently removed from the body.

The envelope 310 can have a shape of a square or rectangle. Other shapes may also be used, such as oval, round, etc. The envelope 310 is advantageously large enough to contact a sufficient area of fatty tissue when expanded. For example, the width of the envelope 310 may be between about 5 cm and about 25 cm in each of two orthogonal dimensions. Other shapes and sizes of envelopes 310 may also be used. The envelope 310 can be formed of any thin, pliable or flexible material that is advantageously biocompatible and not prone to leakage. For example, the envelope 310 can be formed of medical grade, soft elastomers that can allow elastic expansion of the envelope, similar to a balloon that are able to conform in shape to a wide variety of anatomical compartments. The wall of the envelope 310 is advantageously thin enough to facilitate heat exchange across the wall, while providing sufficient mechanical integrity to retain the cooling substance 125 within the envelope 310 and reduce a likelihood of leakage. For example, the envelope 310 can be made using polyethylene, silicone, or another polymer material.

The embodiment of the present invention illustrated in FIGS. 3A and 3B can be used to cool fatty tissue located in certain internal regions of the body, where direct introduction of uncontained fluid into the region may be undesirable. For example, the envelope 310 may be introduced proximal to the perinephrium to cool fatty tissue surrounding the kidneys, proximal to the heart to cool and disrupt fatty tissue there, or proximal to other areas where cooling and/or disruption of fatty tissue is desired.

A catheter 140, 240, 340 used in accordance with embodiments of the present invention can be similar to those used for various peritoneal dialysis procedures. Typical properties of such catheters are described, e.g., in Ash, *Seminars in Dialysis*, vol. 16., no. 4, pp. 323-334 (2003). For example, a typical catheter 140, 240, 340 may be between about 8 cm and about 30 cm in length, and may be straight, curved, or T-shaped. It can be formed of a metal or a metal alloy, silicone, polyurethane, or similar materials. The outer diameter of the catheter 140, 240, 340 can be between about 2 mm and about 4 mm, or preferably between about 2.5 mm and about 3.5 mm. Holes provided in the catheter 140, 240, 340 for allowing the fluid to flow through can be advantageously between about 0.5 mm and 1.5 mm in diameter, or about 1 mm. in diameter. Elongated slits may also be provided instead of or in addition to holes. Such slits can be between about 0.3 mm and about 1 mm wide, and may be between about 2 mm to about 15 mm long, or between about 2 mm and about 5 mm long. The catheter 140, 240, 340 can be provided with one or more cuffs or discs that can improve the seal where the catheter 140, 240, 340 enters the body and/or enters the peritoneal cavity 170.

The fluid 125 used in embodiments of the present invention is advantageously isotonic, nontoxic, and biocompatible, e.g., having a composition that will not cause any adverse effects such as excessive hydration or dehydration when introduced into the abdominal cavity. The fluid 125 is advantageously sterile to reduce any chance of infection. Fluids having compositions similar to those used in conventional peritoneal dialysis procedures may be used. For example, the cooled fluid 125 can be an aqueous solution that may include electrolytes such as sodium, potassium, calcium, magnesium, and organic acid salts such as sodium lactate. The fluid 125 may also include components such as glucose, manitose, or glycols. The fluid 125 can also be provided as a liquid-solid phase-change slurry at or near the freezing temperature of the liquid phase, for example, a flowable slurry of a saline solution containing granules of water ice. The temperature of such a slurry can be adjusted, e.g., by adjusting the composition and volume fraction of the liquid and solid components. The temperature of such a slurry can be substantially stable at or near the phase transition (melting) temperature of the solid phase with respect to heat absorption by the slurry. Heat absorbed by such a slurry can be substantially greater than that absorbed by a simple liquid at a particular temperature or over a narrow temperature range, e.g., a range of a few degrees or less, due to the latent heat of melting of the solid phase.

A vascoconstrictor, e.g., epinephrine or the like, may also be included in the fluid 125, which can help reduce local blood flow in the fatty tissue and thereby increase the cooling effectiveness. Other components of the fluid 125 may include an anesthetic or an anti-inflammatory substance. The pH of the fluid 125 can advantageously be slightly acidic, e.g., having a pH between about 5.0 and about 5.5, or between about 5.2 and about 5.3, although fluids having a pH outside of this range may also be used in certain embodiments.

A broader range of fluid properties and compositions may be used with the embodiments that include an envelope, pouch, or other enclosure 310 as shown in FIGS. 3A and 3B, because such fluid 125 is contained within the envelope or enclosure 310 during the procedure and does not contact bodily tissue directly. The envelope or enclosure 310 can be flexible to facilitate positioning of the envelope or enclosure 310 proximal to the visceral fat. For example, the cooling fluid 125 can be provided as a "slush" or slurry of ethanol and water/ice may be introduced into the envelope 310. Temperature, composition and volume of the slurry introduced into the envelope 310 can be selected to provide a desired amount of cooling of the surrounding tissue by allowing the slurry to remain in the envelope 310 for a particular duration. Such slurry can provide a local temperature that does not vary significantly over time. For example, the enthalpy change of the melting slurry can continue to extract heat from the surrounding tissue while leading to only small changes in the temperature of the slurry itself. As long as a fraction of the slurry remains frozen, the temperature of the proximal tissue can be cooled to a substantially constant temperature. The temperature (or narrow range of temperatures) can be selected based on the composition of the slurry.

The flow rate used in certain embodiments of the present invention may vary depending on the type of cooling procedure performed. For example, a relatively fast flow rate can be used if the cooled fluid 125 is being introduced directly into the abdominal cavity 175, allowed to remain for a predetermined interval, and then drained. Such flow rates can be, for example, between about 200 ml/min and about 500 ml/min. These relatively high flow rates can produce more turbulence within the abdominal cavity 170 and thereby increase the short-term cooling of the fatty tissue by the cooled fluid 125.

In certain embodiments of the invention, a cooling procedure can be provided where the cooled fluid 125 is simultaneously pumped into and withdrawn from the abdominal cavity 170 (e.g., a continuous-flow procedure). Fluid flow rates for such a procedure can advantageously be between about 50 ml/min and about 300 ml/min. Slower flow rates can help avoid excessive cooling by allowing the blood circulation in the body to warm the abdominal organs and the fluid to a greater degree while the cooled fluid 125 is resident in the abdomen. Alternatively, higher flow rates may be used to maintain a relatively constant temperature within portions of the abdominal cavity 170 by continuously introducing cooled fluid 125 and withdrawing it before the body tissues warm it to a significant degree.

Hypothermia effects can optionally be reduced during the exemplary cooling procedures described herein by compensating for the heat transfer away from the body at other sites. For example, a conventional heating pad or other warm object can be applied on the skin surface over the abdomen during all or a portion of the cooling treatment. The warm object advantageously can be provided at a temperature that is approximately at or slightly above normal body temperature. Such surface warming can help to avoid excessive cooling of the skin and abdominal muscles that lie over the abdominal cavity 170, which can also facilitate localization of cooling effects to the visceral fat within the peritoneal cavity. Other sites of the subject's body can also be warmed during the cooling procedure using conventional techniques, to further reduce undesirable hypothermia effects. Such other sites may include portions of the mouth, nasopharynx and/or gastrointestinal tract of the subject, e.g., by introduction of warm air, fluids, or solids either directly or through a catheter or the like, such as a nasogastric tube. The cooling/warming rates and/or cumulative caloric cooling and warming for the visceral fat and distant sites respectively, can be monitored in order to estimate the total heat exchanged with the subject. Adjusting the cooling/warming rates and/or cumulative cooling and warming to be substantially equivalent, can be used as a means of providing or approximating an overall thermal equilibrium for the subject during the procedures described herein.

In certain embodiments, lipid-rich cells of the present invention are adipocytes within visceral fatty tissue. Thus, lipid-rich cells comprising the visceral or omental adipose tissue may be targeted for disruption using the exemplary cooling apparatus 100, 200 and methods of the present invention.

In certain embodiments, lipid-rich cells of the present invention have a total intracellular lipid content of between about 20-99%. In some embodiments, lipid-rich cells of the present invention may have an intracellular lipid content that includes about 20-50% saturated triglycerides, and in other embodiments about 30-40% saturated triglycerides. Intracellular triglycerides include, but are not limited to, saturated fatty acids e.g., myristic, palmitic and stearic acid; monounsaturated fatty acids, e.g., palmitoleic and oleic acid; and polyunsaturated fatty acids e.g., linoleic and linolenic acid.

Lipid-rich cells that may be disrupted and/or reduced using the methods and apparatus of the present invention may be located within abdominal adipose tissue. In certain embodiments, non lipid-rich cells of the present invention have a total intracellular lipid content of less than about 20%, and/or are not disrupted by cooling methods of the present invention. In other embodiments, non-lipid-rich cells of the present invention include cells having an intracellular lipid content comprising less than about 20% highly saturated triglycerides, and in still other embodiments less than about 7-10% highly saturated triglycerides. Non-lipid-rich cells include, but are not limited to, those surrounding the visceral or abdominal fatty tissue, such as cells of the various organs and proximal muscle tissue, as well as those forming the peritoneum itself.

In one embodiment, the temperature of the cooled lipid-rich cells during the exemplary cooling procedures described herein is not less than about $-10°$ C. In another embodiment, the temperature of the lipid-rich cells is between about $0°$ C. and about $24°$ C. In yet another embodiment, the temperature of the lipid-rich cells is between about $0°$ C. and about $15°$ C. The cooling temperatures selected, considered in conjunction with the cooling times, are advantageously cold enough to provide sufficient disruption of the lipid-rich cells and fatty tissue, but warm enough to avoid producing significant damage to other nearby tissues and organs.

In certain embodiments, the total cooling time for the lipid-rich cells is about 10 minutes or greater. Longer cooling times may be used, e.g., durations up to about two hours or more. For example, shorter cooling periods may be used when cooling to lower temperatures, whereas longer cooling periods may be used when cooling to slightly warmer temperatures. The cooling durations selected, considered in conjunction with the cooling temperatures, are advantageously long enough to provide sufficient disruption of the lipid-rich cells and fatty tissue, but short enough to avoid producing significant damage to other nearby tissues and organs.

The cooling temperatures and corresponding durations for the fatty tissue can be selected based on the fatty acid composition of the lipid-rich cells being cooled. In general, both time and temperature can affect the degree of crystallization of the lipids. For example, lipids that don't crystallize immediately at a particular temperature may crystallize after remaining at that same temperature for longer times (e.g., durations that may be greater than an hour, or even greater than several hours). Some of the fatty tissue disruption associated with cooling may also be related to the shape of the crystals formed, rather than just the presence of crystallization, which may be dependent on fatty acid composition. Disruption of fatty tissue may also be achieved by cooling under certain conditions even if crystallization of the fatty tissue is not observed.

In yet another embodiment, the controller 130 can be configured to provide an oscillating temperature profile to the tissue region that includes the lipid-rich cells. Such pulsed cooling followed by brief periods of warming can be generated by controlling the temperature and flow rate of the cooled fluid introduced into the tissue region being cooled, and may reduce likelihood of generating collateral damage to non-lipid-rich cells. For example, such temperature can oscillate between, e.g., about $37°$ C. and about $-10°$ C., or between about $-5°$ C. and about $30°$ C. Even more preferably, the temperature range of the lipid-rich cells can oscillate between about $0°$ C. and about $20°$ C. or about $25°$ C. Such cooling and warming cycles can be provided, e.g., by alternately pumping colder and warmer fluid 125 into the tissue region through the catheter 140, 240 as described herein. For example, the cooling may be achieved by alternating longer cooling cycles with shorter warming cycles, such that the fatty tissue is effectively cooled and disrupted while minimizing or avoiding damage to the surrounding tissue.

Cooling of internal body tissues as described herein may induce vasoconstriction. Blood circulation within the internal organs facilitates stabilization of the local temperature close to normal body temperature. Vasoconstriction within the internal tissue and organs when they are cooled can reduce local blood flow and further facilitate cooling of the adipose tissue to temperatures below body temperature.

Without being bound by theory, it is believed that the rate of formation of crystals in lipid-rich cells can be altered by the application of pressure during the cooling process. Sudden crystallization, rather than a slow accumulation of crystals, may cause greater damage to the lipid-rich cells. Application of pressure to cooled adipose tissue may also force the movement of the crystals within the lipid-rich cells, enhancing the damage to the bilayer membrane. Furthermore, different compartments of the subcutaneous adipose tissue have different viscosities. In general, the viscosity is enhanced at colder temperatures (e.g., those particularly close to the point of phase change). Because the phase change for lipid-rich cells occurs at higher temperatures than non lipid-rich cells, non-uniform tension lines can form within the subcutaneous adipose tissue upon the application of pressure. It is believed that pronounced damage may occur within these tension lines.

Accordingly, in further embodiments of the invention, cooling of the lipid-rich tissue can be accompanied by mechanical or other disruption of the fatty tissue, e.g., through application of acoustic fields that may be either constant or oscillating in time. For example, one or more transducers may be introduced into the region of tissue being cooled through the catheter, and signals provided to them to produce mechanical oscillations and disruption of the fatty tissue. Alternatively, ultrasound energy can be provided from one or more sources of such energy, e.g., piezoelectric transducers, provided in contact with an outer surface of the subject's body during the cooling procedure. Such ultrasound energy can optionally be focused to the approximate depth of the fatty tissue being cooled to further disrupt the tissue.

Although the exemplary apparatus described herein and illustrated in FIGS. 1-3 are illustrative of the basic components of a system suitable for use with embodiments of the present invention, the specific architecture shown should not be considered limiting because many variations of the hardware configuration are possible without departing from the present invention.

Exemplary studies have been performed to examine the feasibility, consequences, and mechanisms of visceral fat tissue reduction by cryolipolysis. For example, freshly collected murine perigonadal fat tissue samples obtained from mice were compressed between a glass slide and a cooling device for examination. The temperature in the cooling device was controlled by a circulating water bath, and the temperature in the tissue sample was monitored using a digital thermometer. The tissue samples were heated to 37° C. and then gradually cooled.

Figure 4A:
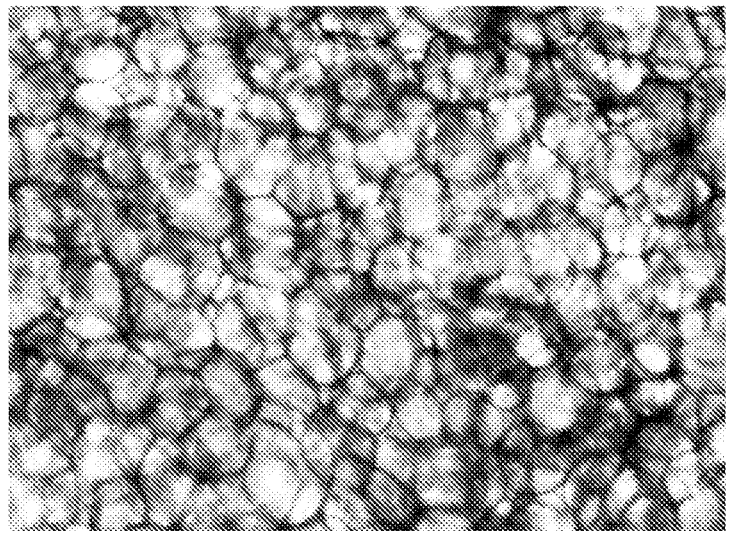
FIG. 4A is a bright-field image of murine perigonadal tissue.
Figure 4B:
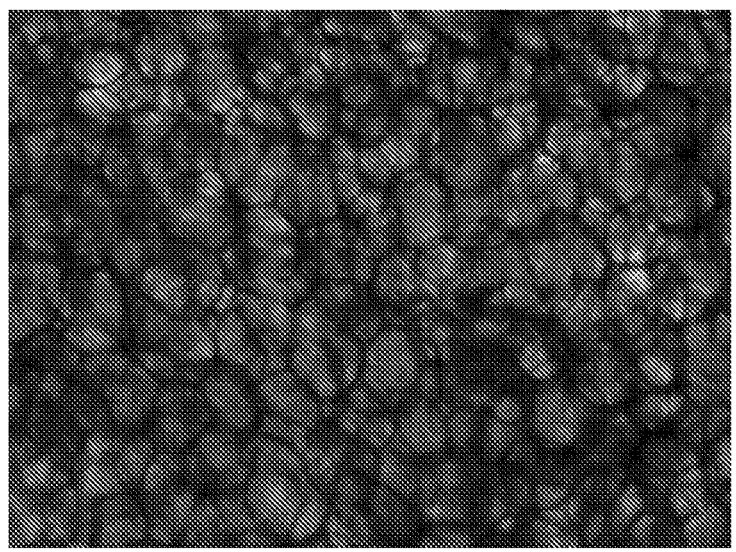
FIG. 4B is a cross-polarized image of the perigonadal tissue shown in FIG. 4A that has been heated to 37° C.
Figure 4C:
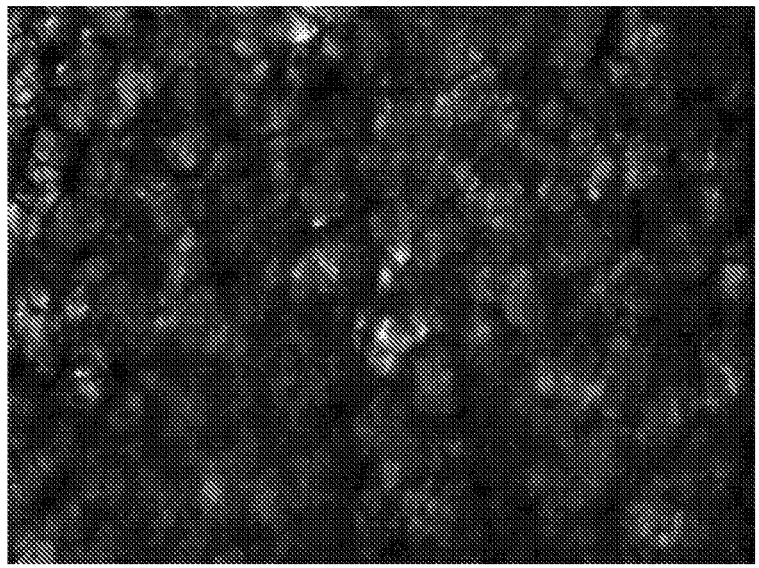
FIG. 4C is a cross-polarized image of the perigonadal tissue shown in FIG. 4A that has been cooled to 10° C.
Figure 4D:
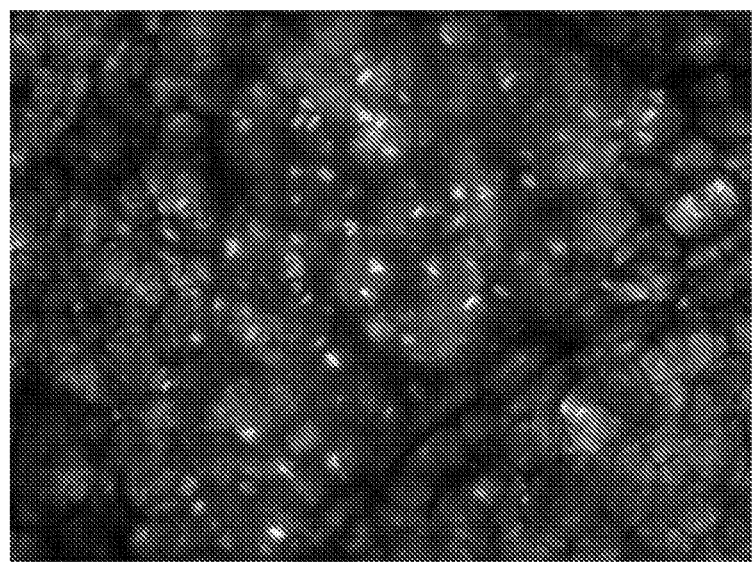
FIG. 4D is a cross-polarized image of the perigonadal tissue shown in FIG. 4A that has been cooled to 5° C.

Anisotropic crystals became detectable under cross-polarized light when the tissue was cooled to 5° C. FIG. 4A shows the perigonadal fat tissue as seen under bright-field microscopy. In FIG. 4B, the same tissue sample is shown at 37° C. as imaged by cross-polarized light. Lipids appear to be in the liquid phase and no crystals were observed at this temperature. When cooled to 10° C., no apparent crystals were observed in the tissue samples, as shown in FIG. 4C. At 5° C. anisotropic crystals become clearly detectable under cross-polarized light. These crystals are shown in FIG. 4D as slightly lighter areas. Each image field shown in FIGS. 4A-4D is 450 µm wide.

Visceral fat cooling was also studied in live mice to examine the physical and physiological effects of exemplary cryolipolysis treatment. Male, 8 week old C57Bl/6J mice were maintained on a 45% kcal % fat diet (HFD). After 2 weeks of HFD feeding, perigonadal (visceral) fat pads were exposed and cooled to 3° C. for 5 minutes using a contact cooling device. Fat pads of other mice were heated to 37° C. instead of cooling, and untreated mice were also used as controls. Body weights were recorded weekly.

Figure 5A:
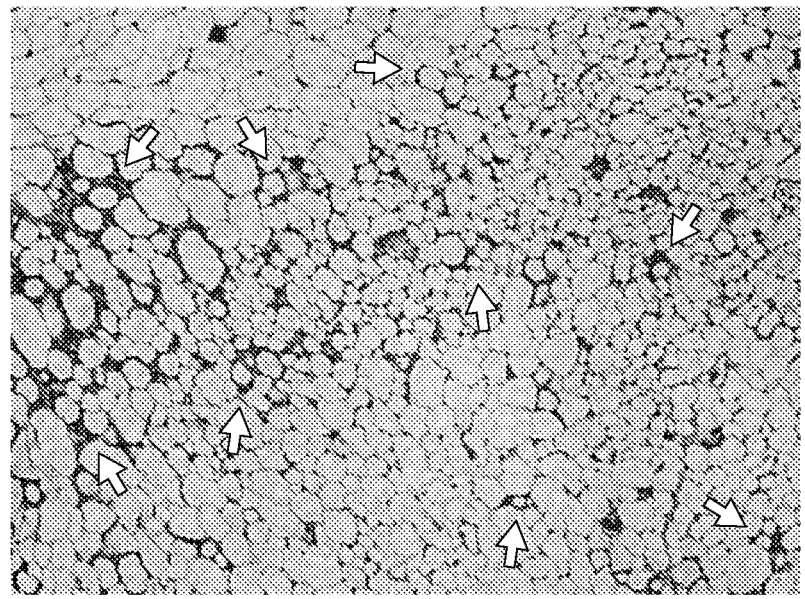
FIG. 5A is an image of perigonadal tissue that was cooled to 3° C. and removed from the mouse three weeks after cooling.
Figure 5B:
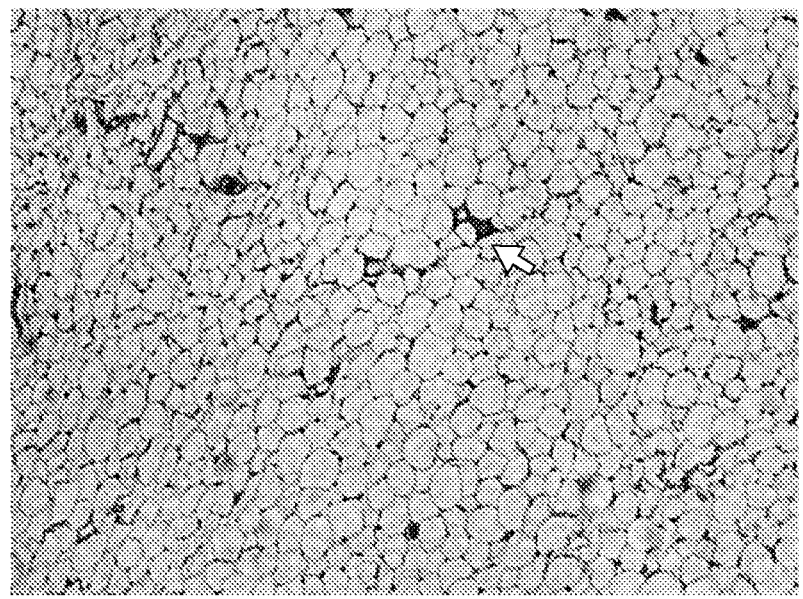
FIG. 5B is an image of perigonadal tissue that was warmed to 37° C. and removed from the mouse three weeks after warming.

Three weeks after the cooling/heating procedure, perigonadal fat pads were collected from some of the mice, fixed in 4% formaldehyde, embedded in paraffin, sectioned, and then stained with hematoxylin and eosin. The fat tissue that was cooled to 3° C., shown in FIG. 5A, was observed to contain substantial regions resembling the "crown-like" structures of macrophage syncytia. These structures, indicated by the white arrows in FIG. 5A, are characteristically found around necrotic fat cells in obese animals, and may be important for fat tissue remodeling. In contrast, crown-like structures were observed to be few in number and sparsely present in the fat pads that were warmed to 37° C., as shown in FIG. 5B. This difference in observed histologies suggests that macrophage infiltration and remodeling activities in fat tissue may be increased by cooling. The images in FIGS. 5A and 5B are each about 1.2 mm wide.

Mice in the different groups had similar body weights prior to the cooling procedures. Body weight fell significantly for the mice with treated fat pads in the first week post-cooling/warming. In the subsequent weeks, the untreated group showed a higher mean body weight as compared to the two groups with treated fat pads, but the difference was not statistically significant. Body weights were similar throughout the experiment between the two groups that had treated fat pads, as shown in FIG. 6A.

Figure 6A:
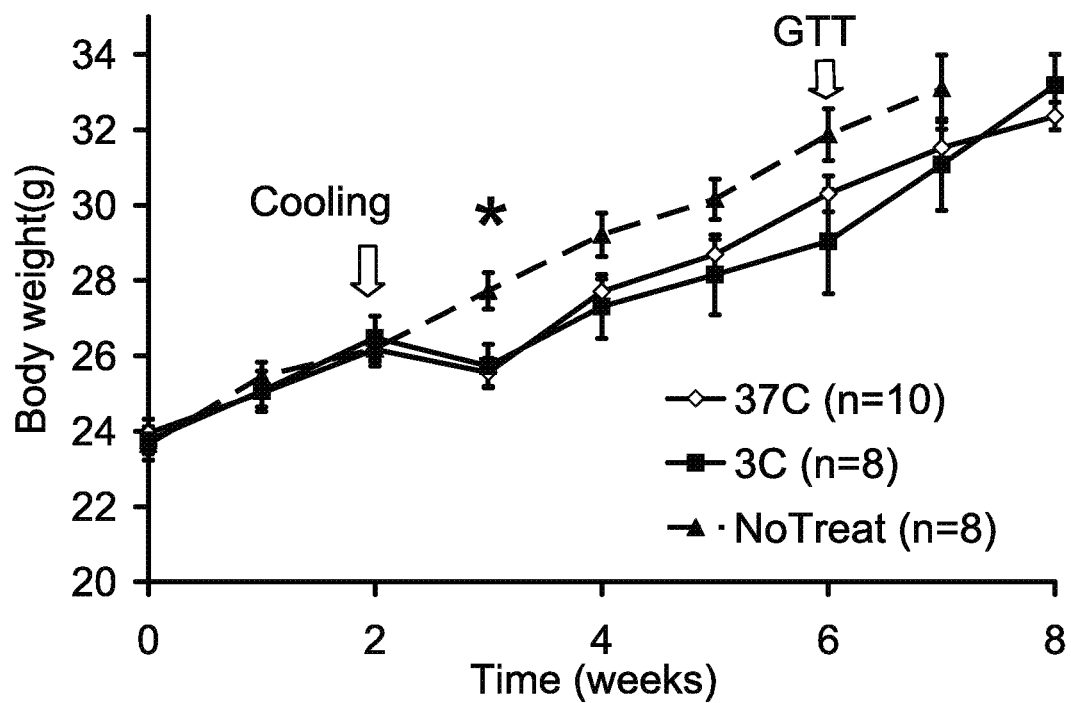
FIG. 6A is a plot of data for three groups of mice indicating body weight as a function of time.
Figure 6B:
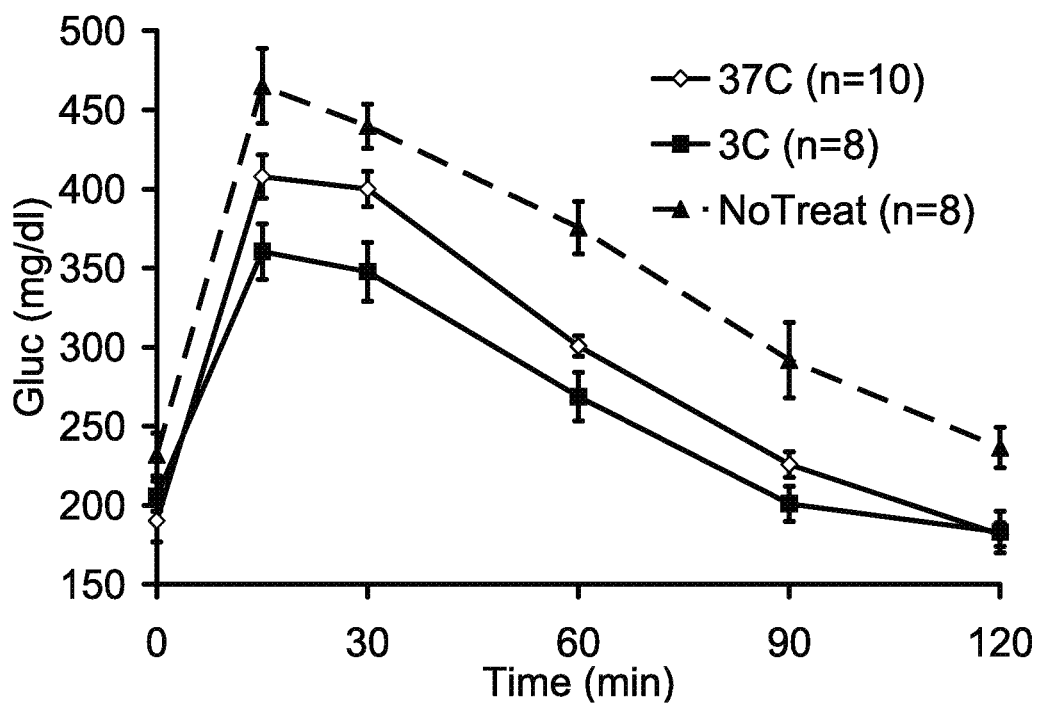
FIG. 6B is a plot of results of glucose tolerance tests (GTT) that were performed on three groups of mice four weeks after fat pads of two groups of mice were heated or cooled.
Figure 6C:
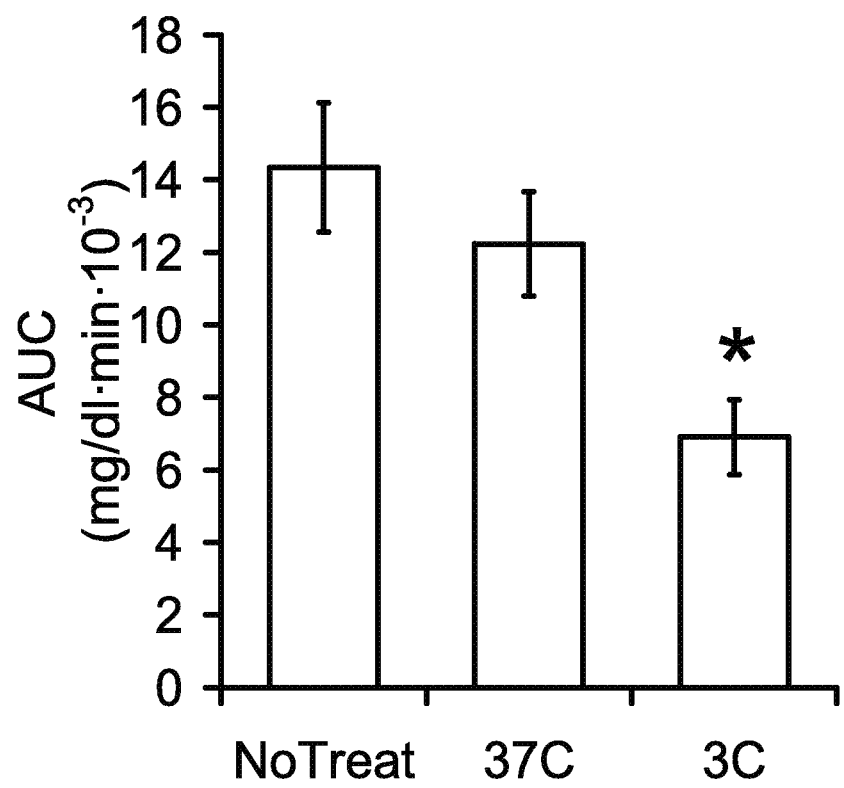
FIG. 6C is a plot of the areas under the curve (AUC) for the glucose tolerance test results shown in FIG. 6B.

Glucose tolerance tests (GTT) were performed on all the mice at the time indicated by the GTT arrow in FIG. 6A, i.e., four weeks after the fat pads were treated. Glucose tolerance appeared to be significantly improved in the group of mice whose fat pads were cooled to 3° C., as compared to the group of mice whose fat pads were warmed to 37° C. These results are shown in FIG. 6B. The area under the curve (AUC) for the GTT results depicted in FIG. 6B, after adjusting for fasting glucose levels, are shown in FIG. 6C. These results indicate a significant difference ($p<0.05$) in glucose tolerance between the mice whose fat pads were cooled to 3° C. and the other two groups of mice (controls and fat pads warmed to 37° C.). Multi-sample comparisons were performed using one-way ANOVA. Between-sample comparisons were evaluated using an unpaired t-test. The untreated group exhibited elevated fasting glucose and impaired glucose tolerance as compared to both treated groups of mice, as indicated by the GTT results shown in FIGS. 6B and 6C.

The difference between the mice with fat pads warmed to 37° C. and the untreated control group also suggests that aspects of the procedure (other than cooling) may also have damaged the fat tissue. For example, excessive pressure on the fat tissue during the contact cooling or warming may have mechanically disrupted some cells.

These results suggest that cooling of visceral fat in mice can improve glucose metabolism. Similar beneficial effects may be obtainable in humans, e.g., using the exemplary tissue cooling methods and apparatus described herein. Such effects may be produced by cooling to slightly warmer temperatures, e.g., temperatures greater than the 3° C. used for one group of mice, for longer periods of time.

Figure 7:
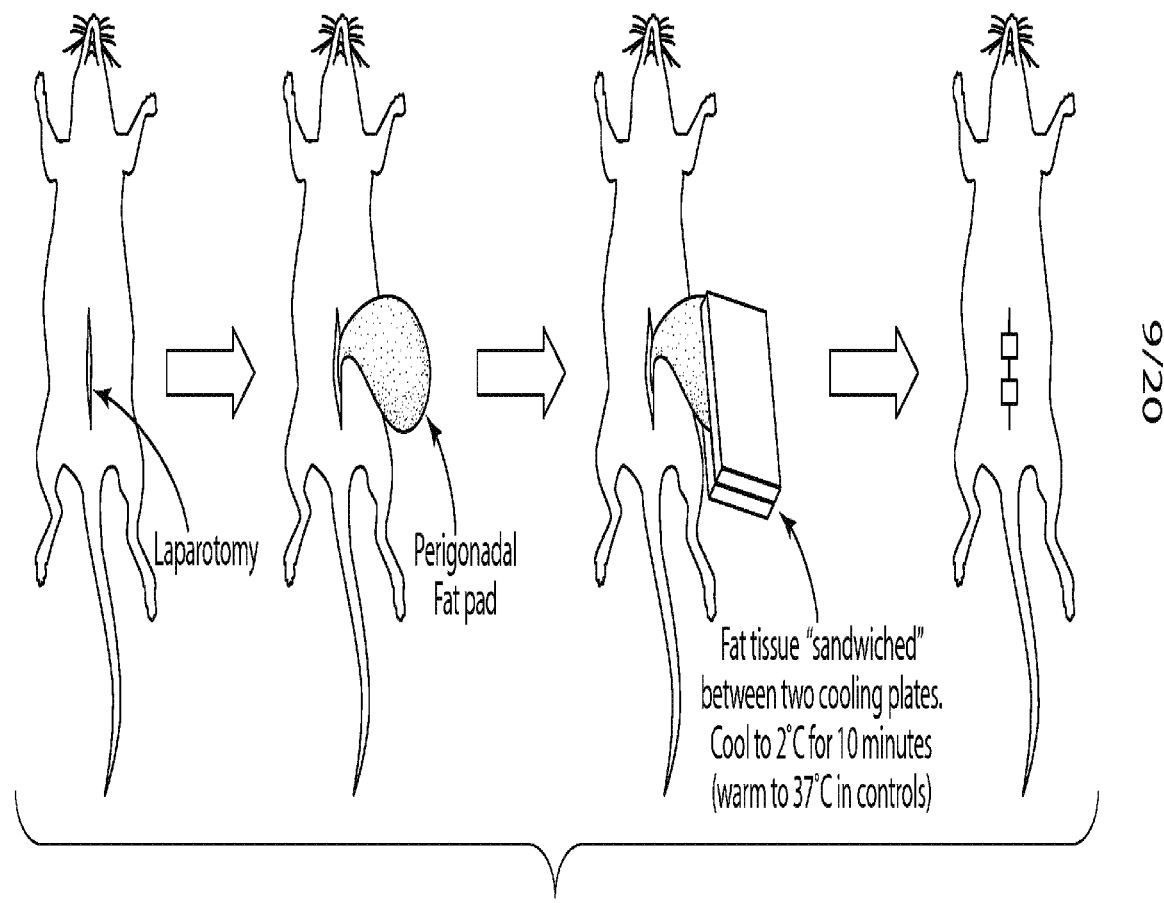
FIG. 7 is a schematic illustration of the procedure used to cool or warm the visceral fat pad in mice.

In a further study on live mice to examine the physical and physiological effects of visceral fat cooling, a group of 32 male mice were given a high-fat (45 kcal %) diet (HFD) starting at 7 weeks of age. After 2 weeks of HFD feeding, perigonadal (visceral) fat pads were surgically exposed and cooled to 2° C. for 10 minutes in one group of 16 mice using a contact cooling device. This cooling procedure is illustrated schematically in FIG. 7. Fat pads of a control group of the 16 other mice were exposed in a similar manner, but warmed to 37° C. instead of cooling (substantially maintaining normal body temperature in the exposed pads). This procedure was carried out to isolate the results of cooling the visceral fat pads while replicating the procedure of exposing the fat pads in the two groups. The core temperature of all mice in both groups were maintained by external heating and monitored to ensure consistency between the groups. Body weights were recorded weekly.

Figure 8A:
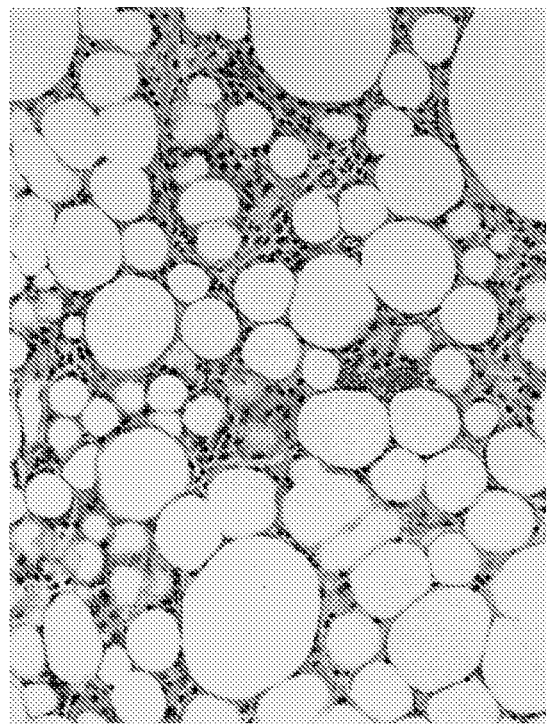
FIG. 8A is an image of perigonadal tissue that was cooled to 2° C. for 10 minutes and removed from the mouse one week after cooling.
Figure 8B:
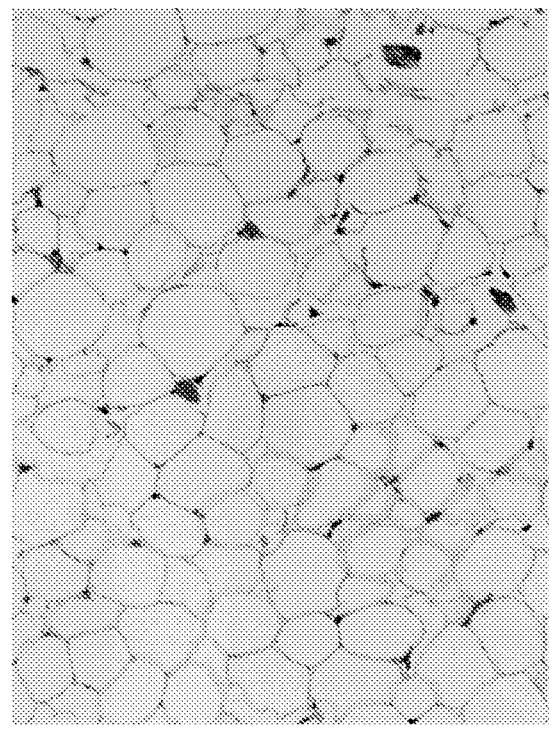
FIG. 8B is an image of perigonadal tissue that was warmed to 37° C. for 10 minutes and removed from the mouse one week after warming.

One week after the cooling/heating procedure, perigonadal fat pads were collected from some of the mice in both groups, fixed in 4% formaldehyde, embedded in paraffin, sectioned, and then stained with hematoxylin and eosin. The fat tissue that was cooled to 2° C., shown in FIG. 8A, was observed to exhibit an inflammatory response and some disruption of the visceral fat structure. In contrast, the fat pads that were warmed to 37° C., shown in FIG. 8B, did not exhibit such disruption of the fatty tissue. This difference in observed histologies further suggests that disruption and tissue remodeling activities in fat tissue may be induced by cooling of the fatty tissue.

Figure 9:
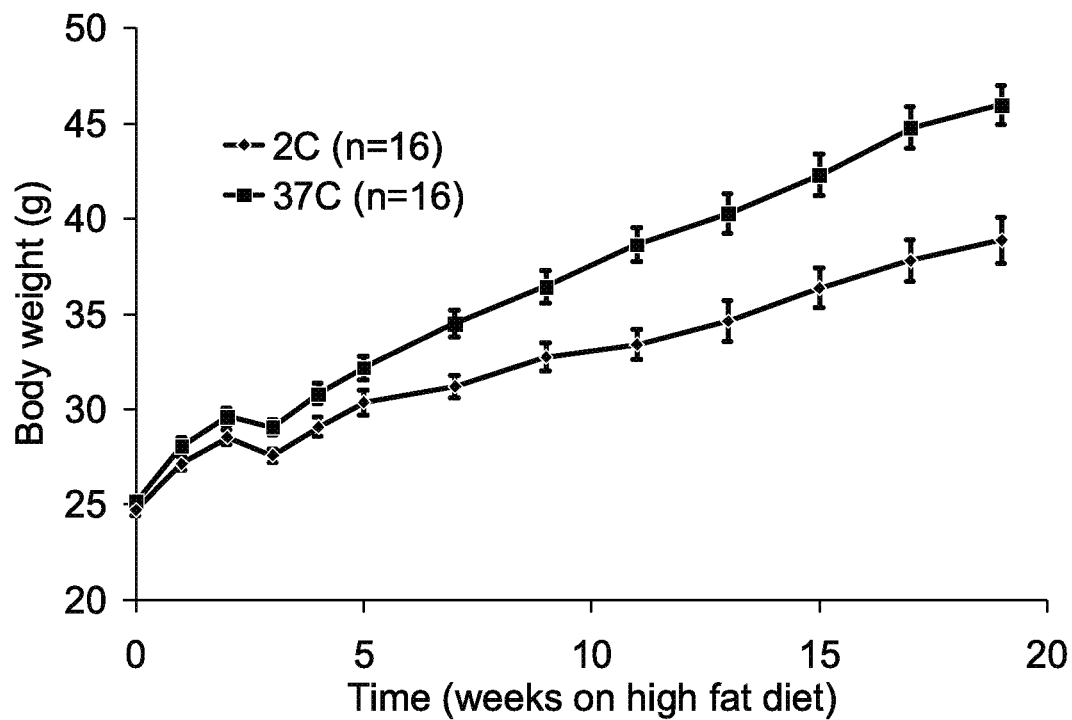
FIG. 9 is a plot of data for two groups of mice on a high-fat diet indicating body weight as a function of time.

The mice in the two groups (the test group having visceral fat cooled to 2° C. for 10 minutes and the control group with visceral fat warmed to 37° C.) had similar body weights prior to the cooling procedures. All mice were maintained on the high-fat diet for 20 weeks. The body weights of the test group increased more slowly than that of the control group, and the body weights were similar within each of the two groups of mice throughout the experiment, as indicated by the weight data and bars indicating the standard error of the mean values in the data shown in FIG. 9.

Figure 10:
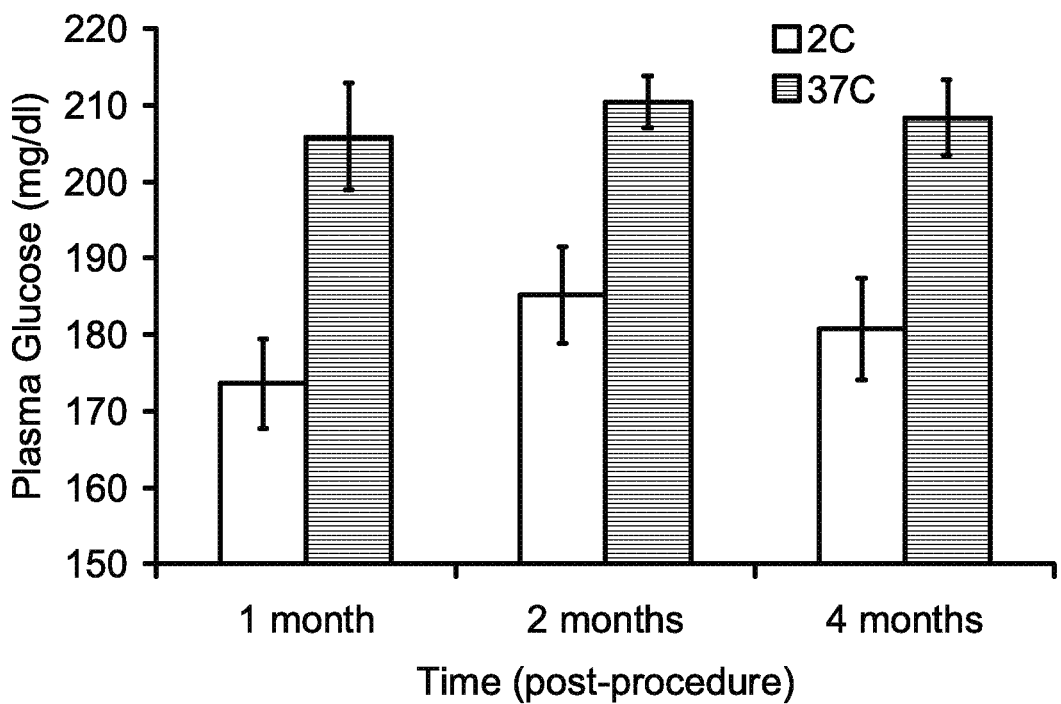
FIG. 10 is a plot of plasma glucose level data for two groups of mice on a high-fat diet measured at various times after exposing and warming or cooling the visceral fat pad.
Figure 11:
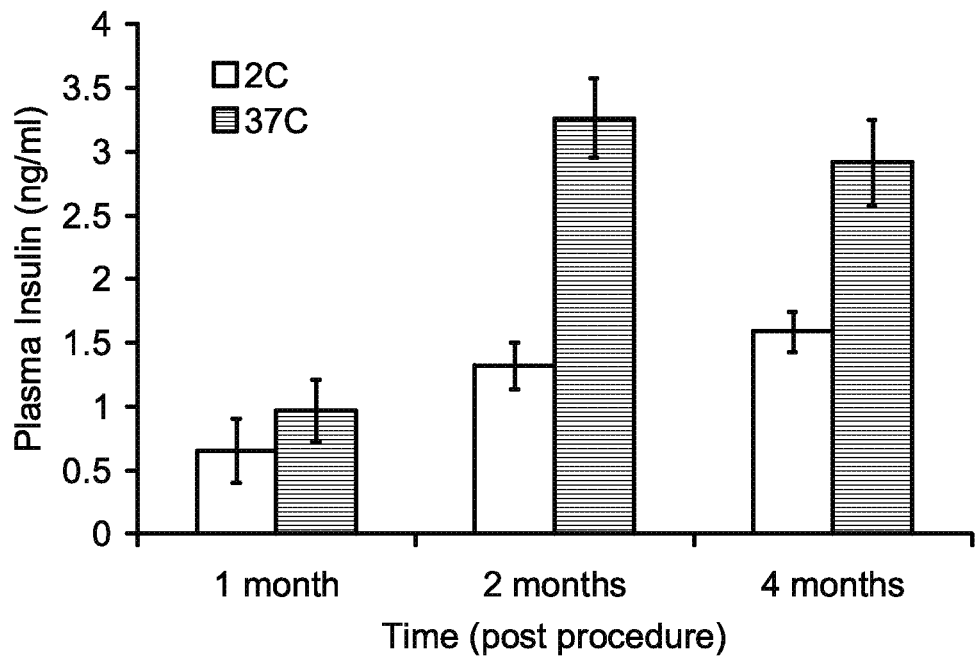
FIG. 11 is a plot of plasma insulin level data for two groups of mice on a high-fat diet measured at various times after exposing and warming or cooling the visceral fat pad.

Glucose and insulin fasting levels were also tested periodically in the two groups of mice. As indicated by the plots shown in FIGS. 10 and 11, both the fasting glucose levels and fasting insulin levels were significantly lower in the test group of mice that were subjected to visceral fat cooling than in the control group that had the visceral fat warmed to 37° C. These results further suggest that disruption of the visceral fat by cooling can provide physiological benefits.

Figure 12:
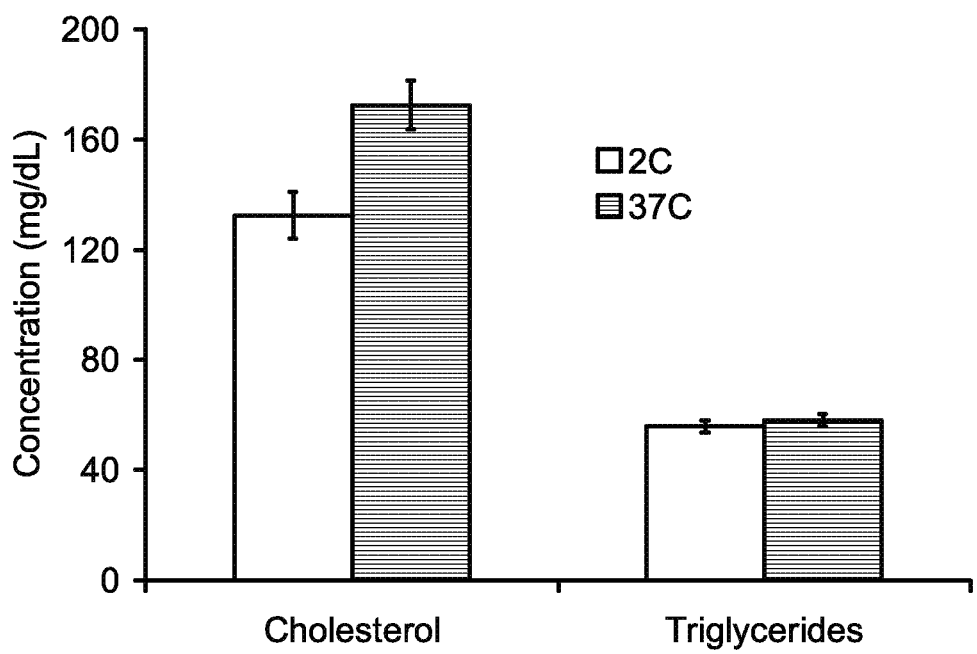
FIG. 12 is a plot of plasma cholesterol and triglycerides levels for two groups of mice on a high-fat diet measured 4 months after exposing and warming or cooling the visceral fat pad.

Blood cholesterol levels were measured in the two groups of mice 4 months after the cooling/warming of the visceral fat was performed in the two groups. The blood cholesterol was significantly lower (more than 20% lower, on average) in the test group of mice with the cooled visceral fat as compared to the test group of mice that had the warmed visceral fat. The levels of triglycerides in the blood were substantially the same in both groups of mice. These data on blood cholesterol and triglyceride levels are shown in FIG. 12.

Figure 13:
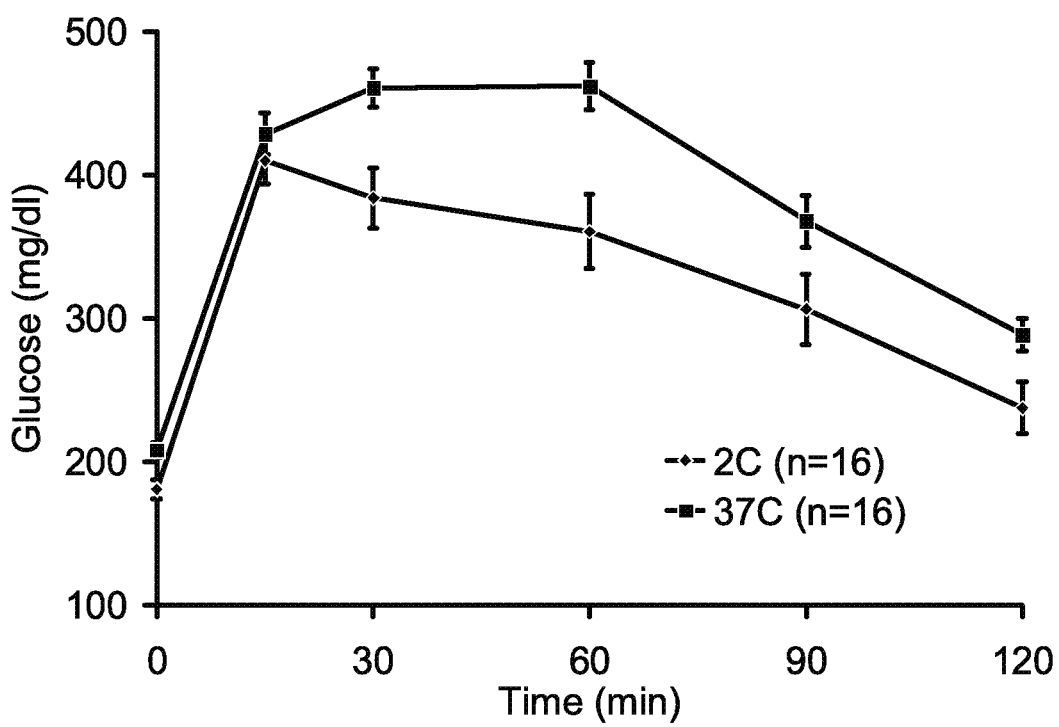
FIG. 13 is a plot of results of glucose tolerance tests (GTT) that were performed on two groups of mice four months after fat pads of the two groups of mice were heated or cooled.

Glucose tolerance tests (GTTs) and insulin tolerance tests (ITTs) were performed on all the mice four months after the fat pads were treated in both groups. These tests were performed by giving each mouse a bolus dose of glucose or insulin, and then following the blood level of each substance over the next 2 hours. The GTT data shown in FIG. 13 indicate that glucose levels decreased more rapidly and were generally lower in the test group of mice than in the control group after the initial short-term rise. Accordingly, glucose tolerance appeared to be significantly improved in the test group of mice whose fat pads were cooled to 2° C. for 10 minutes, as compared to the control group of mice whose fat pads were warmed to 37° C.

Figure 14:
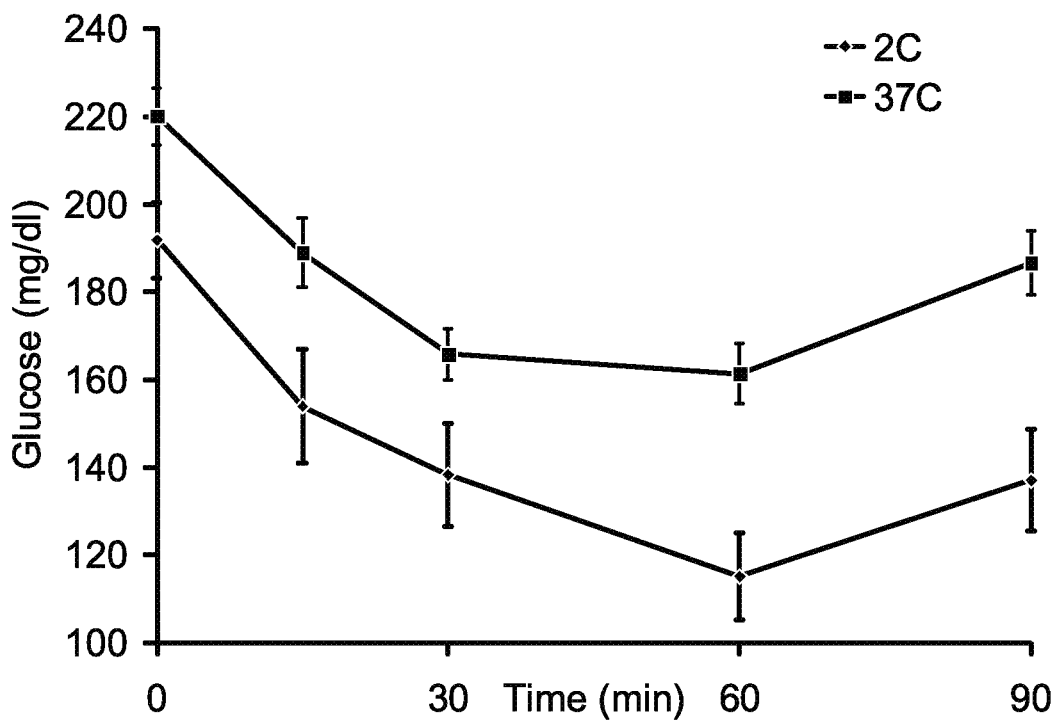
FIG. 14 is a plot of results of insulin tolerance test s(ITT) that were performed on two groups of mice four months after fat pads of the two groups of mice were heated or cooled.

The ITT data, shown in FIG. 14, indicate that blood glucose levels decreased more rapidly in the test group of mice and remained lower than in the control group after administration of a dose of insulin to each of the mice in the two groups. These data suggest that insulin sensitivity was increased in the mice that were subjected to cooling of the visceral fat pads than in the control group that did not experience such cooling of the visceral fat.

Figure 15:
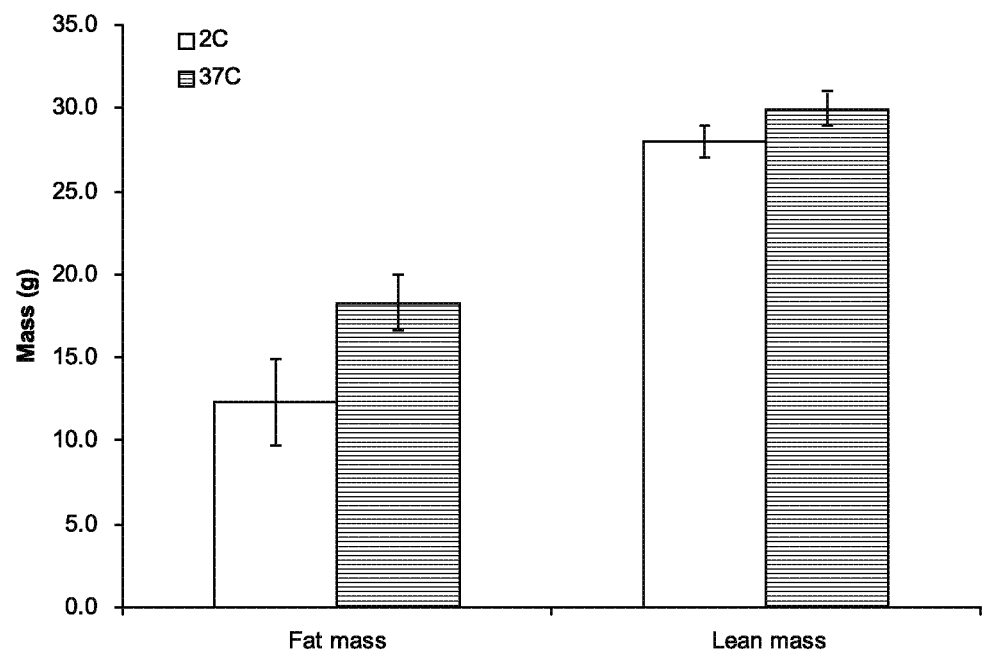
FIG. 15 is a plot of fat and lean body mass measurements that were obtained from two groups of mice five months after fat pads of the two groups of mice were heated or cooled.

Both lean and fat body mass were measured in the two groups of mice using proton magnetic spectroscopy analysis performed 5 months after the visceral fat pads were exposed and cooled to 2° C. for 10 minutes (test group) or warmed to 37° C. for 10 minutes (control group). The body mass results, shown in FIG. 15, indicate that the fat body mass (left side) was significantly lower in the test group as compared t the control group, whereas the lean body mass (right side) remained similar for both groups of mice.

A similar set of experiments were also performed on a smaller group of genetically obese ob/ob mice. Visceral fat pads were surgically exposed and cooled to 2° C. for 10 minutes in a test group of 6 mice, and the fat pads of a control group of 5 mice were warmed to 37° C. for 10 minutes, as described above and illustrated schematically in FIG. 7. Body weights of all mice in the two groups were recorded weekly.

Figure 16:
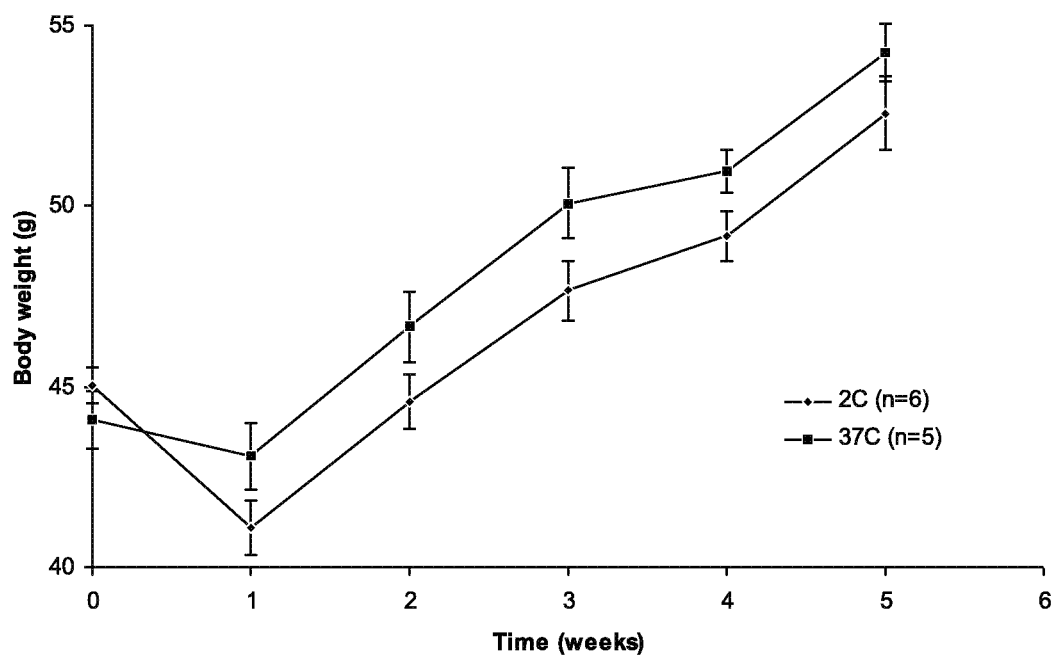
FIG. 16 is a plot of data for two groups of genetically obese mice indicating body weight measured at various times after exposing and warming or cooling the visceral fat pad.

The average body weight of the mice in the test group remained lower than that of the mice in the control group, as shown in FIG. 16. There appeared to be an initial significant drop in body weight of the test group during the first week after the visceral fat was cooled, followed by increase in average body weight over time (as the mice matured) that roughly paralleled the weight increase of the control group. The difference in average body appeared to be maintained between the two groups of mice as they grew.

Figure 17:
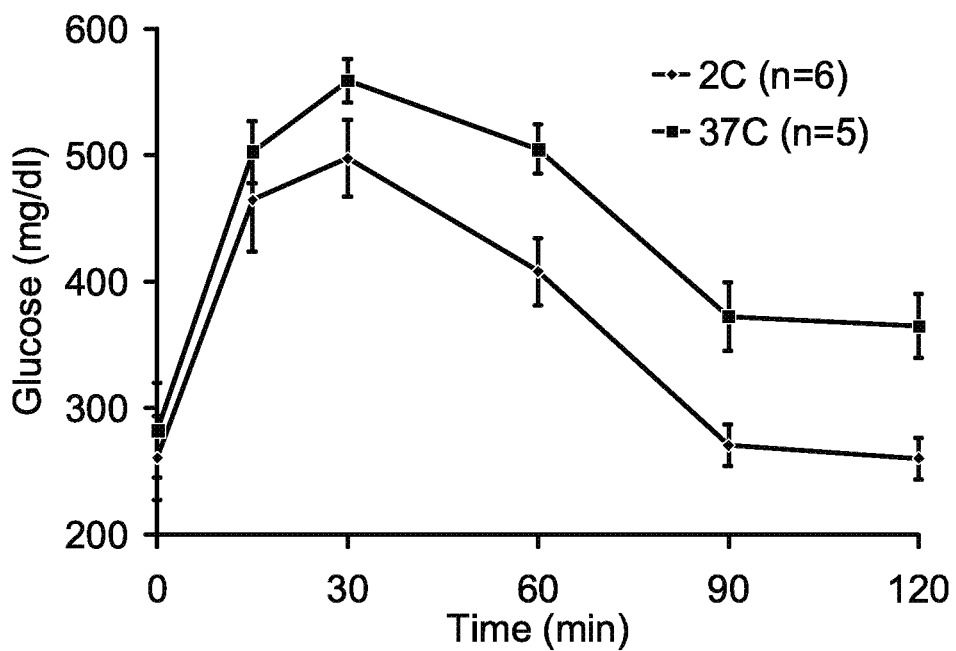
FIG. 17 is a plot of results of glucose tolerance tests (GTT) that were performed on two groups of genetically obese mice four weeks after fat pads of the two groups of mice were heated or cooled.

Glucose tolerance tests performed 4 weeks after the visceral fat pads were exposed indicate that glucose tolerance improved in the test group of mice that had their visceral fat pads cooled, as compared to the control group. These results are shown in FIG. 17, and appear similar to the GTT results shown in FIG. 13 for the two groups of mice that were maintained on a high-fat diet as described herein above.

Observation of the various groups of mice subjected to different cooling/warming procedures as described above suggests that cooling of visceral fat (e.g., to a temperature of 2° C. or 3° C. for 5 or 10 minutes) can help protect the animals against diet-induced or genetic obesity and insulin resistance, as compared to the control groups: The mice that were subjected to visceral fat cooling exhibited lower body weight, lower fasting glucose and insulin levels, lower cholesterol, improved glucose tolerance, and improved insulin sensitivity as compared to the mice that were not subjected to such fat cooling.

Certain studies were also performed to assess differences in crystallization behavior between subcutaneous and visceral fat in pigs. Samples of subcutaneous and visceral (omental) fat were obtained from pig specimens. Each fatty tissue was homogenized and centrifuged. Lipids (present in the top layer) were then collected and filtered through a 0.45 μm filter. The lipid samples were subjected to various cooling treatments, and then imaged using cross-polarized light microscopy.

Figure 18:
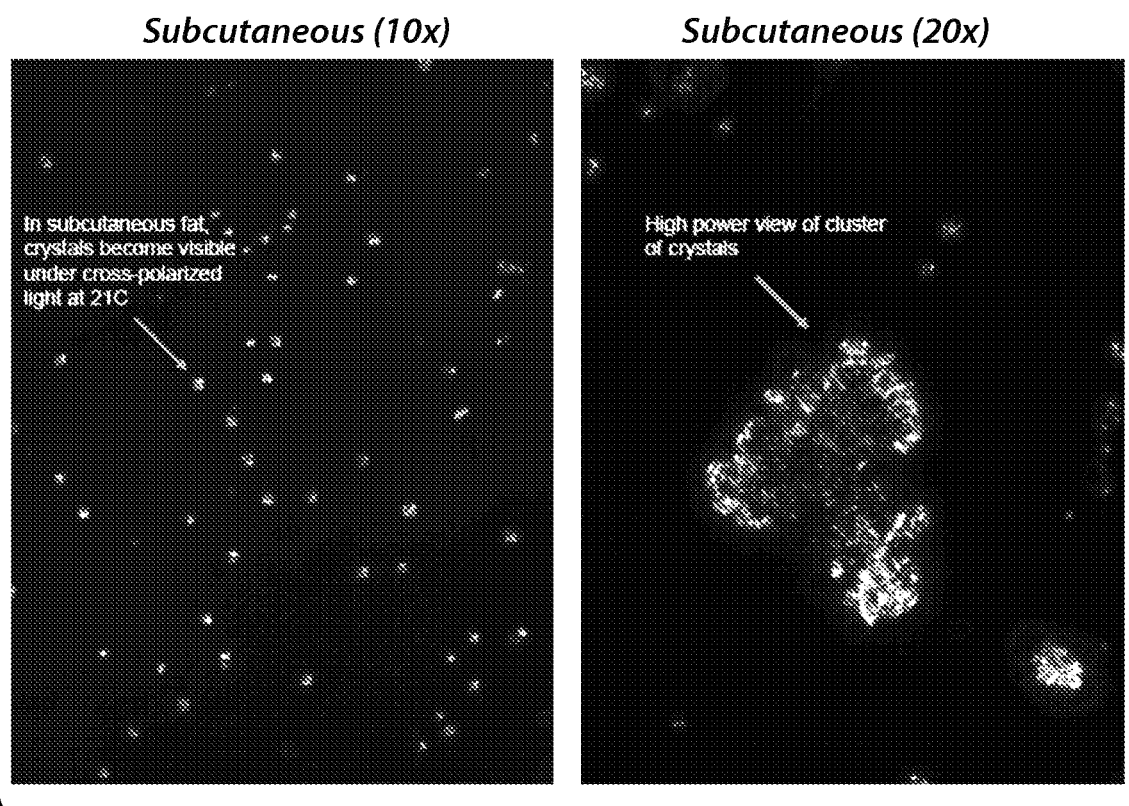
FIG. 18 shows cross-polarized images at 10× and 20× of crystals forming at 21° C. in lipids obtained from subcutaneous fat of a pig.
Figure 19:
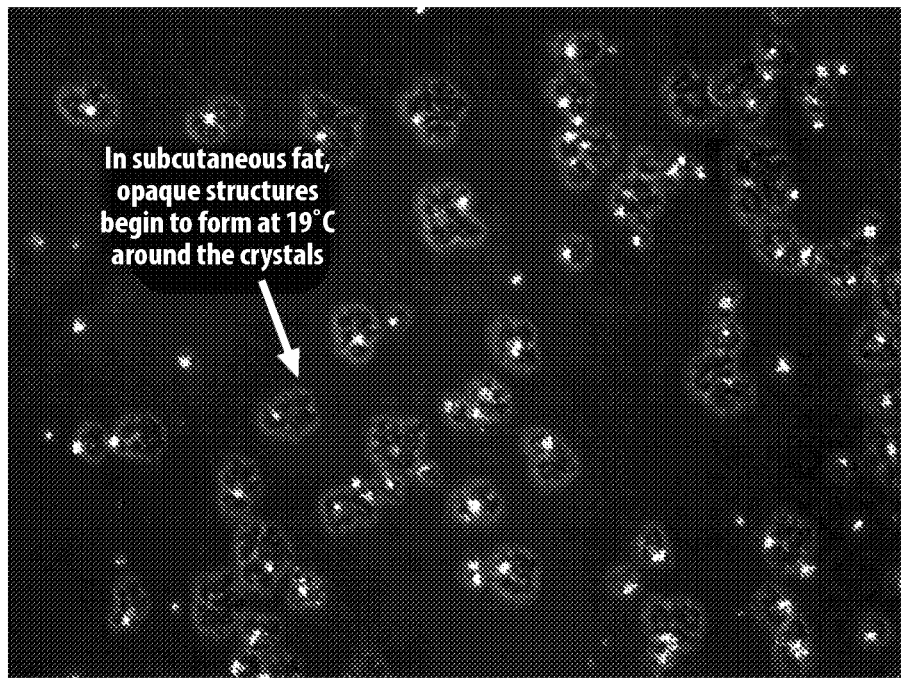
FIG. 19 shows a cross-polarized image at 10× of crystals forming at 19° C. in lipids obtained from subcutaneous fat of a pig.

Initially, the lipid samples (obtained from both subcutaneous and visceral fat) were heated to 45° C. The cross-polarized images were uniformly dark, because the lipids were entirely in the liquid state at this temperature. When cooled to 21° C., the lipids obtained from the subcutaneous fat exhibited crystals that could be observed under the cross-polarized light. These crystals are shown in FIG. 18 at two different magnifications (10× and 20×). Opaque structures were observed to form around the crystals in the lipids obtained from subcutaneous fat when it was cooled to 19° C., as shown in FIG. 19.

Figure 20:
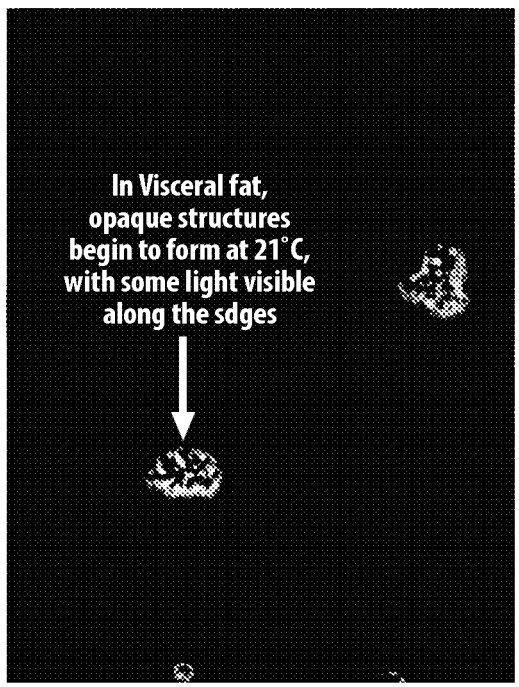
FIG. 20 shows a cross-polarized image at 10× and a plane-polarized image at 20× of crystals forming at 21° C. in lipids obtained from visceral fat of a pig.
Figure 20:
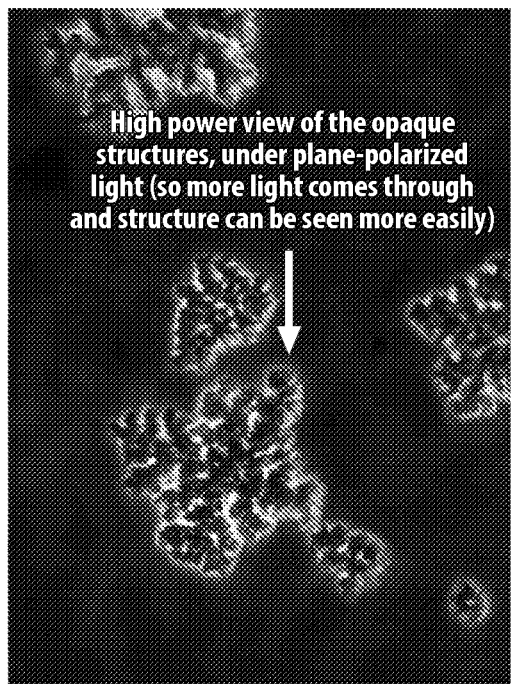

The lipids obtained from visceral fat also exhibited crystallization when cooled to 21° C., as shown in FIG. 20. The right side of FIG. 20 is an image at 20× obtained using plane-polarized light, which allows more light to penetrate the sample to reveal more details of the crystal structure.

Figure 21:
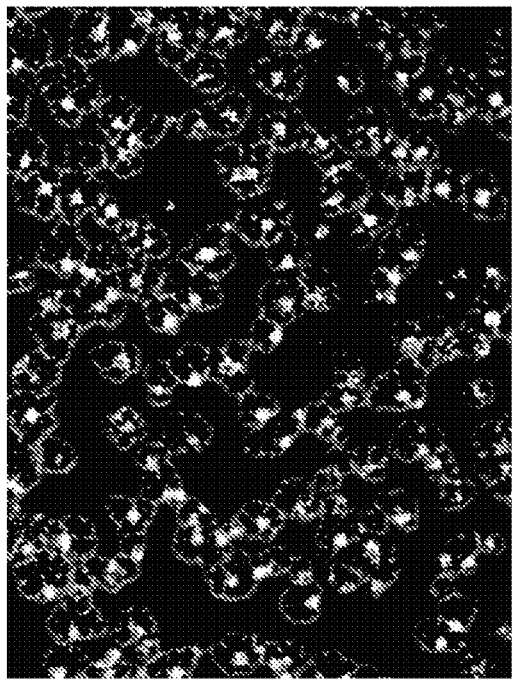
FIG. 21 shows cross-polarized images at 10× of crystals forming at 13° C. in lipids obtained from subcutaneous and visceral fat of a pig.
Figure 21:
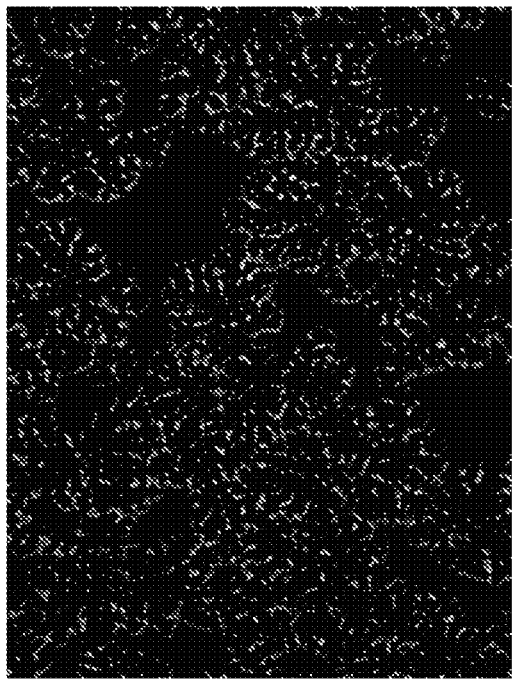

A comparison of the crystals observed in the subcutaneous and visceral fat lipids when cooled to 13° C. is shown in FIG. 21. The crystals formed in lipids obtained from the two types of fat exhibit different morphologies, suggesting differences in their crystallization behavior.

Figure 22:
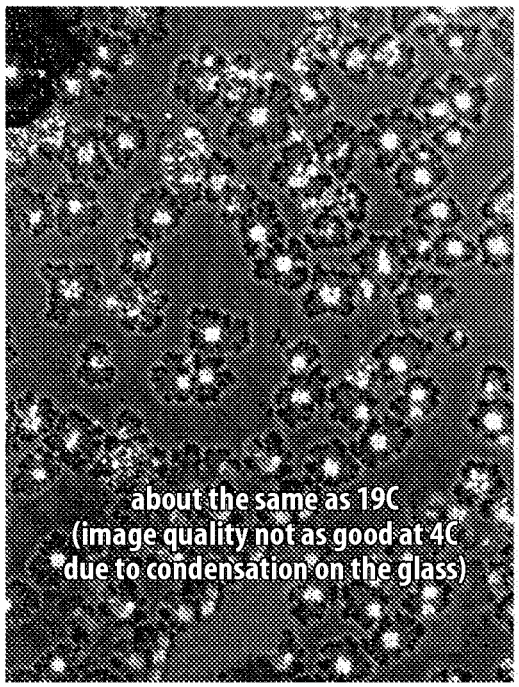
FIG. 22 shows cross-polarized images at 10× of crystals forming at 4° C. in lipids obtained from subcutaneous and visceral fat of a pig.
Figure 22:
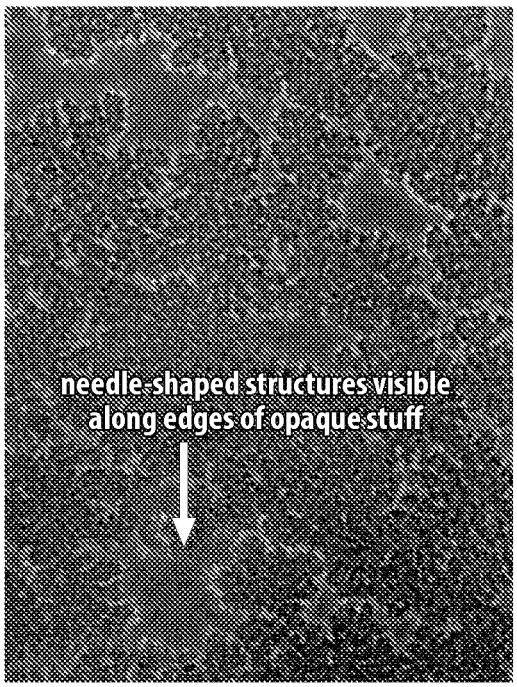

A comparison of the crystallization at 4° C. observed in the subcutaneous and visceral fat lipids is shown in FIG. 22. The subcutaneous fat crystals at 4° C. appear similar to the crystals formed at 13° C. (shown in the left-hand portion of FIG. 21). The image of subcutaneous fat crystals in the left-hand portion of FIG. 22 appears to have slightly less clarity arising from condensation on the glass holding the sample.

Figure 23:
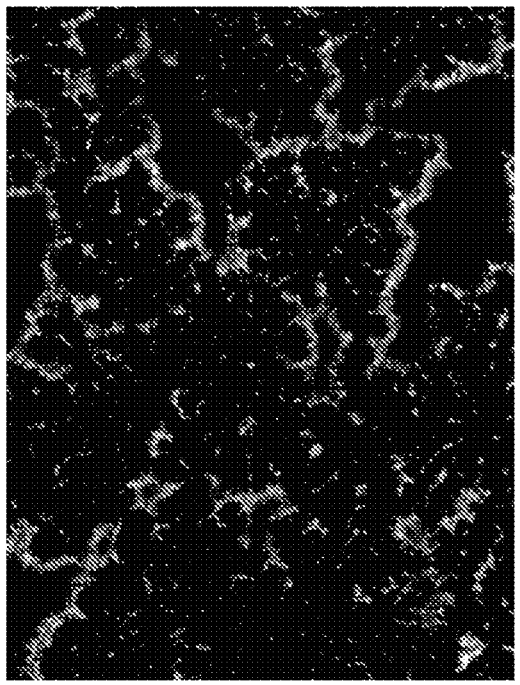
FIG. 23 shows cross-polarized images at 20× of crystals forming at 4° C. in lipids obtained from visceral fat of a pig.
Figure 23:
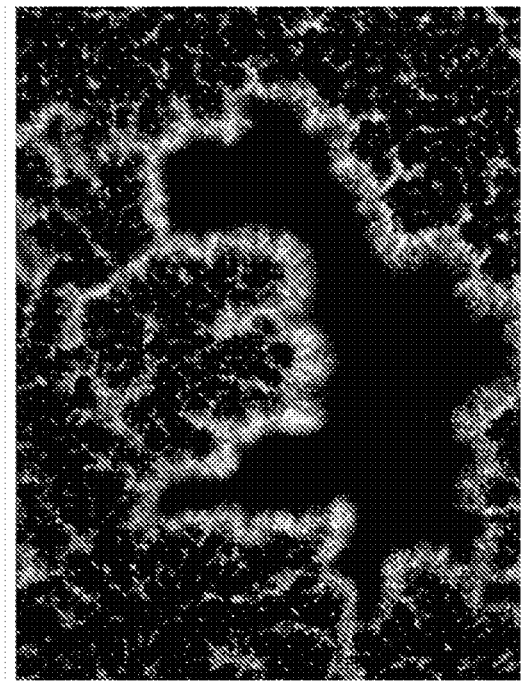
Figure 24A:
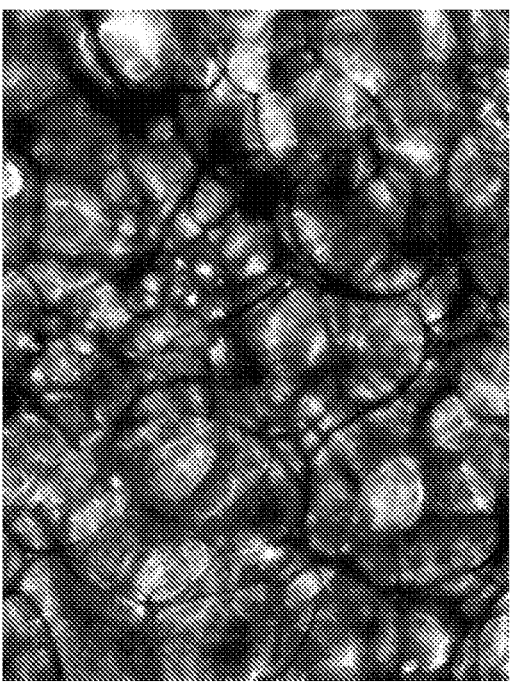
FIG. 24A shows cross-polarized images at 10× of human subcutaneous and visceral fat samples held at 37° C.
Figure 24A:
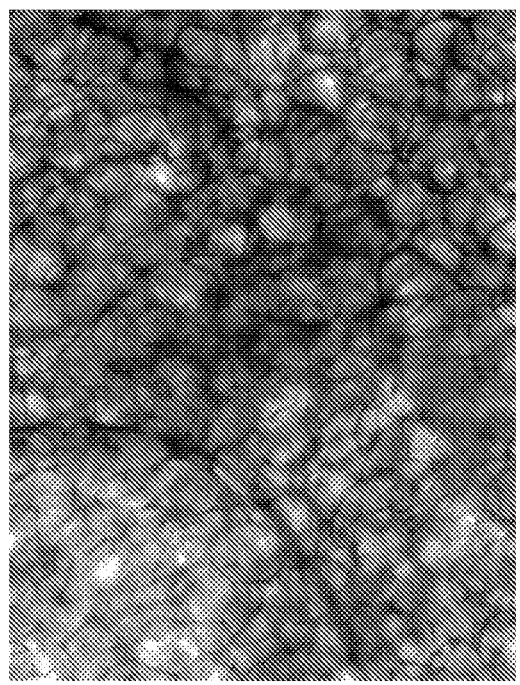
Figure 24B:
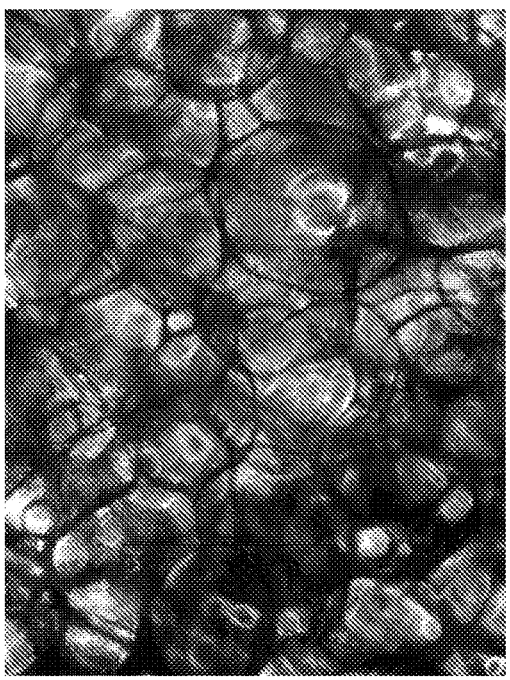
FIG. 24B shows cross-polarized images at 10× of human subcutaneous and visceral fat samples cooled to 20° C.
Figure 24B:
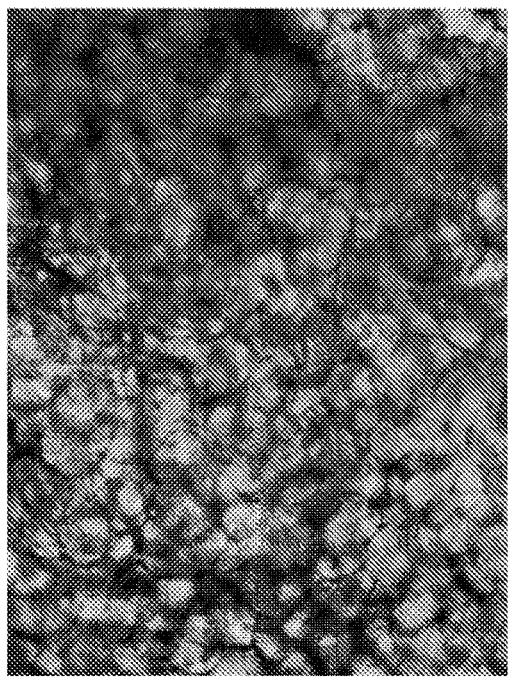
Figure 24C:
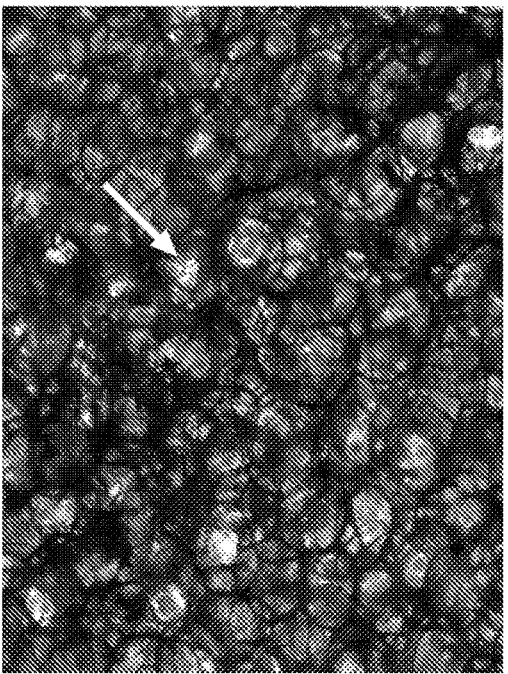
FIG. 24C shows cross-polarized images at 10× of human subcutaneous and visceral fat samples cooled to 15° C., indicating crystallization within the fat.
Figure 24C:
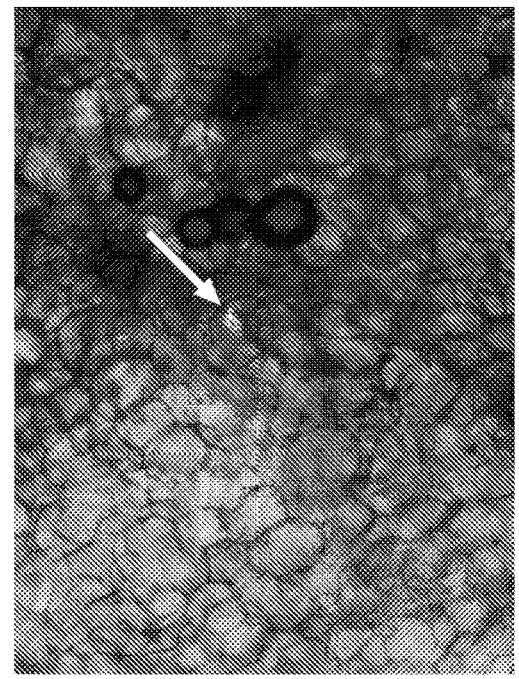
Figure 24D:
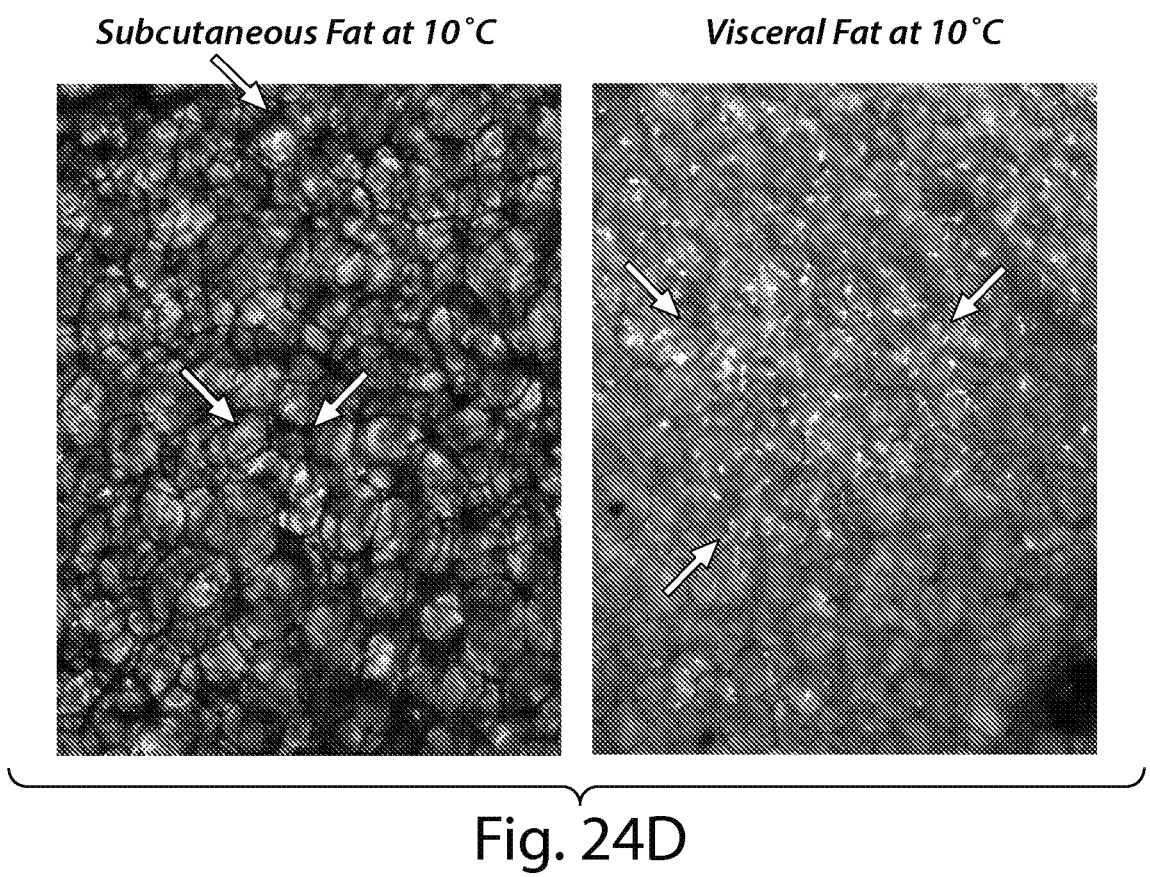
FIG. 24D shows cross-polarized images at 10× of human subcutaneous and visceral fat samples cooled to 10° C., indicating crystallization within the fat.

The visceral fat crystals formed at 4° C., shown in the right-hand portion of FIG. 22, exhibit some needle-like structures along the edges of the opaque regions. These visceral fat lipid crystals at 4° C. are shown at higher magnification in FIG. 23. The presence of the needle-like structures in the visceral fat crystals suggests that visceral fat cells may be more susceptible to disruption by cooling than subcutaneous fat cells at a particular temperature.

Further studies were performed on human subcutaneous and omental (visceral) fat samples that were obtained from discarded surgical specimens. Both types of fat samples were cooled to various temperatures and observed using cross-polarized light microscopy. Using such imaging procedure, the lipids in a liquid state will appear dark, whereas any crystals that form will appear lighter.

Cross-polarized images of subcutaneous fat samples (left side) and visceral fat samples (right side) that were held at temperatures of 37° C., 20° C., 15° C., and 10° C., each image obtained at a magnification of 10×, are shown in FIGS. 24A-24D, respectively. No significant crystallization was observed at 37° C. or 20° C. in either of the two types of fat samples, as indicated by the uniformly dark images in FIGS. 24A and 24D, respectively. Some crystallization (light spots) was observed in both subcutaneous and visceral fat when cooled to 15° C., as indicated by the white arrows in FIG. 24C. Further crystallization was observed in booth types of fat when cooled to 10° C., some of them indicated by the white arrows in FIG. 24D. These preliminary results suggest that both visceral fat and subcutaneous fat can exhibit similar crystallization behavior when cooled, and that crystallization can be observed in both types of fat when cooled to temperatures of about 15° C. or lower. These results suggest that crystallization and disruption of human visceral fat can be achieved by cooling the fat to a temperature of about 15° C. or lower. Disruption of the visceral fat, which may also damage or reduce the amount of such fat present in the body, may also be achievable when cooling the fat to slightly higher temperatures, e.g., temperatures of about 20° C., even though evidence of crystallization may not be visible.

Accordingly, disruption of visceral fat tissue may be achieved by cooling of the fat tissue, similar to the disruption of subcutaneous fat tissue by cooling as described, e.g., in U.S. Pat. No. 7,367,341. Significant differences in fatty acid composition between subcutaneous and visceral fat in humans have been reported in the literature (Garaulet M, et al., Int J Obes, 2006; 30(6): 899-905). Accordingly, there may be differences in crystallization characteristics (e.g., shape of crystals, extent of tissue disruption, etc) between subcutaneous and visceral fat in humans. Cooling parameters used with embodiments of the present invention should be selected to provide sufficient disruption of fatty tissue without generating significant damage to other surrounding tissue, e.g., body organs.

A number of embodiments of the present invention have been described herein. Nevertheless, it will be understood that various modifications may be made without departing from the spirit and scope of the invention. Further, each of the patents and/or patent applications cited in this text, as well as each document or reference cited in each of these applications and patents (including during the prosecution of each issued patent) ("application cited documents"), and each of the PCT and foreign applications or patents corresponding to and/or claiming priority from any of these applications and patents, and each of the documents cited or referenced in each of the application cited documents, are hereby expressly incorporated herein by reference. More generally, all documents or references cited in this invention ("herein-cited references"), as well as each document or reference cited in each of the herein-cited references (including any manufacturer's specifications, instructions, etc.), are hereby expressly incorporated herein by reference.

The invention claimed is:

1. A method for selective disruption of lipid-rich visceral fat in a non-infant human subject comprising:
   applying a cooling substance at a temperature of less than about 20° C. to a location proximal to the subject's visceral fat to reduce the temperature within a local region containing the visceral fat and to selectively disrupt at least a portion of the visceral fat of said region;
   wherein the cooling substance comprises at least one of: an aqueous solution, an isotonic solution, a saline solution, and a vasoconstrictor.

2. The method of claim 1, wherein the cooling substance is provided within the abdominal cavity of the subject.

3. The method of claim 1, further comprising removing at least a portion of the cooling substance from the location after a predetermined time interval.

4. The method of claim 3, wherein the predetermined time interval is at least about 5 minutes.

5. The method of claim 3, wherein the predetermined time interval is at least about 10 minutes.

6. The method of claim 1 wherein the cooling substance is a liquid.

7. The method of claim 6, wherein the cooling substance comprises an aqueous solution.

8. The method of claim 7, wherein the aqueous solution is at least one of an isotonic solution or a saline solution.

9. The method of claim 6, wherein the cooling substance comprises a vascoconstrictor.

10. The method of claim 6, wherein the cooling substance is provided at a temperature that is less than about 15° C.

11. The method of claim 6, wherein the cooling substance is provided at a temperature that is less than about 10° C.

12. The method of claim 6, wherein the cooling substance comprises a solid-liquid slurry capable of undergoing a phase change at a substantially stable temperature.

13. The method of claim 1, further comprising inserting a catheter through at least a portion of the subject's body such that a distal end of the catheter is proximal to visceral fat of the subject, and wherein applying the cooling substance comprises providing the cooling substance through a lumen in the catheter.

14. The method of claim 13, further comprising measuring a temperature of at least one of the cooling substance applied to the location or a portion of the cooling substance that is withdrawn from the location after a particular time interval.

15. The method of claim 1, further comprising heating a portion of the subject's body to reduce cooling of a portion of the body away from the local region containing the visceral fat cells.

16. The method of claim 14, further comprising providing a further quantity of the cooling substance to the location, wherein at least one of the temperature or the amount of the further quantity of the cooling substance is selected based on the measured temperature.

17. The method of claim 1, further comprising removing a portion of the cooling substance from the location while introducing a further quantity of the cooling substance at a temperature of less than about 20° C. to the location.

18. The method of claim 17, wherein at least one of the temperature, the amount, or the flow rate of the further quantity of the cooling substance is selected based on a temperature of the removed portion of the cooling substance.

19. An apparatus for cooling a local region of tissue of a non-infant human subject containing visceral fat, comprising:
- a reservoir configured to hold a cooling substance;
- a catheter comprising at least one lumen, wherein the catheter is configured to be inserted into the subject such that at least a portion of the catheter is proximal to the local region of tissue; and
- a conduit configured to facilitate passage of the cooling substance from the reservoir to the local region of tissue.

20. The apparatus of claim 19, wherein the conduit is connected to the at least one lumen to facilitate passage of the cooling substance therethrough.

* * * * *